US008679854B2

(12) United States Patent
Park et al.

(10) Patent No.: US 8,679,854 B2
(45) Date of Patent: Mar. 25, 2014

(54) FLUORESCENT DYE-LABELED GLUCOSE BIOPROBE, SYNTHESIS METHOD AND USAGE THEREOF

(75) Inventors: Seung Bum Park, Seoul (KR); Myung Haing Cho, Seoul (KR); Hyang Yeon Lee, Seoul (KR); Jong Min Park, Seoul (KR)

(73) Assignee: SNU & DB Foundation, Seoul (KR)

( * ) Notice: Subject to any disclaimer, the term of this patent is extended or adjusted under 35 U.S.C. 154(b) by 742 days.

(21) Appl. No.: 12/532,913

(22) PCT Filed: Dec. 21, 2007

(86) PCT No.: PCT/KR2007/006713
§ 371 (c)(1),
(2), (4) Date: Sep. 24, 2009

(87) PCT Pub. No.: WO2008/117918
PCT Pub. Date: Oct. 2, 2008

(65) Prior Publication Data
US 2010/0105149 A1    Apr. 29, 2010

(30) Foreign Application Priority Data
Mar. 26, 2007 (KR) .................. 10-2007-0029334

(51) Int. Cl.
*G01N 21/76* (2006.01)
(52) U.S. Cl.
USPC ........... 436/172; 424/9.6; 536/17.4; 536/17.9
(58) Field of Classification Search
None
See application file for complete search history.

(56) References Cited

U.S. PATENT DOCUMENTS 6,989,140 B2    1/2006    Tidmarsh et al.

FOREIGN PATENT DOCUMENTS

WO    WO2007/100392 A2 *    9/2007    ............ A61B 10/00

OTHER PUBLICATIONS

International Search Report of PCT/KR2007/006713, dated Mar. 31, 2008.
Written Opinion of the International Searching Authority of PCT/KR2007/006713, dated Mar. 31, 2008.
Cheng et al. "Near-Infrared Fluorescent Deoxyglucose Analogue for Tumor Optical imaging in Cell Culture and Living Mice." Bioconjugate Chem. vol. 17, 2006, pp, 662-669.
Zhang et al. "Metabolic imaging of tumors using intrinsic arid extrinsic fluorescent markers." Biosensors and Bioelectronics, vol. 20, 2004, pp. 643-650.
Natarajan et al. "Glucose uptake of single *E. coli* cells grown in glucose-limited chemostat cultures." Journal of Microbiological Methods, vol. 42, 2000, pp. 87-96.
Lloyd et al. "Examining Glucose Transport in Single Vascular Smooth Muscle Cells with a Fluorescent Glucose Analog." Physiological Research, vol. 48, 1999, pp. 401-410.
Yamada et al. "Measurement of Glucose Uptake and Intracellular Calcium Concentration in Single, Living Pancreatic β-Cells."Journal of Biological Chemistry, vol. 275(29), Jul. 21, 2000, pp. 22278-22283.

(Continued)

*Primary Examiner* — Robert Xu
(74) *Attorney, Agent, or Firm* — Hamre, Schumann, Mueller & Larson, P.C.

(57) ABSTRACT

The present invention relates to a fluorescent dye-labeled glucose analog, and a synthesis method and usage of the same, and more particularly, to novel glucose α and β anomers in which a fluorescent dye is labeled by O-1-glycosylation, an asymmetric synthesis method of the anomers, a molecular bioimaging method of the anomers, and a screening method of curing or preventing drugs for diseases related to glucose metabolism.

4 Claims, 19 Drawing Sheets

(56) References Cited

OTHER PUBLICATIONS

Bhattacharyya et al. Fluorescent analogs of UDP-glucose and their use in characterizing substrate binding toxin A from *Clostridium difficile*. Eur. J. Biochem., vol. 269, 2002, pp. 3425-3432.

Mosmann "Rapid Colorimetric Assay for Cellular Growth and Survival: Application for Proliferation and Cytotoxicity Assays." Journal of Immunological Methods, vol. 65, 1983, pp. 55-63.

Li et al. "Synthesis and Antimalarial Activity of Artemisinin Derivatives Containing an Amino Group." J. Med. Chem. vol. 43, 2000, pp. 1435-1640.

Trester-Zedlitz et al. "A Modular Cross-Linking Approach for Exploring Protein Interactions." J. Am. Chem. Soc., vol. 125(9), 2003, pp. 2416-2425.

Campbell et al, "UDP-Glucose Analogues as Inhibitors and Mechanistic Probes of UDP-Glucose Dehydrogenase." J. Org. Chem, vol. 64, 1999, pp. 9487-9492.

Maier et al. "Synthesis of Antisense Oligonucleotides Conjugated to a Multivalent Carbohydrate Cluster for Cellular Testing." Bioconjugate Chem. vol. 14, 2003, pp. 18-29.

Fazio et al. "Synthesis of Sugar Arrays in Microtiter Plate." J. Am. Chem. Soc. vol. 124, 2002, pp. 14397-14402.

Ye et al. "Polyvalent Carbocyanine Molecular Beacons for Molecular Recognitions." J. Am. Chem. Cos. vol. 126, 2004, pp. 7740-7741.

Conti et al. PET and [$^{18}$F]-FDG in Oncology: A Clinical Update. Nuclear Medicine &. Biology, vol. 23, 1996, pp. 717-735.

Yorimitsu et al. "Ultra-rapid Synthesis of $^{15}$O-labeled 2-Deoxy-D-glucose for Positron Emission Tomography (PET)." Angew. Chem. Int. Ed. vol. 44, 2005, pp. 2708-2711.

Som et al. "A Fluorinated Glucose Analog, 2-fluro-2-deoxy-D-glucose (F-18): Nontoxic Tracer for Rapid Tumor Detection." The Journal of Nuclear Medicine, vol. 21(7), 1980, pp. 670-675.

Czernin et al. "Positron Emission Tomography Scanning: Current and Future Applications." Annu Rev. Med. vol. 53, 2002, pp. 89-112.

Hoh et al. "Cancer Detection with Whole-Body PET Using 2-[18F]Fluoro-2-Deoxy-D-Glucose." Journal of Computer Assisted Tomography, vol. 17(4) Jul./Aug. 1993, 2 pages.

Yoshioka et al. "Intracellular Fate of 2-NBDG, a Fluorescent Probe for Glucose Uptake Activity, in *Escherichia coli* Cells." Biosci. Biotech. Biochem, vol. 60(11), 1996, pp. 1899-1901.

Yoshioka et al. "A novel fluorescent derivative of glucose applicable to the assessment of glucose uptake activity of *Escherichia coli*." Biochimica et Biophysica Acta, 1289, 1996, pp. 5-9.

Zhang et al. "Pyropheophorbide 2-Deoxyglucosamide: A New Photosensitizer Targeting Glucose Transporters." Bioconjugate Chem. vol. 14, 2003, pp. 709-714.

\* cited by examiner

FLUORESCENT DYE-LABELED GLUCOSE BIOPROBE, SYNTHESIS METHOD AND USAGE THEREOF

FIELD OF THE INVENTION

The present invention relates to a fluorescent dye-labeled glucose analog, and a synthesis method and usage of the same, and more particularly, to novel glucose α and β anomers in which a fluorescent dye is labeled by O-1-glycosylation, an asymmetric synthesis method of the anomers, a molecular bioimaging method of the anomers, and a screening method of curing or preventing drugs for diseases regarding glucose metabolism.

BACKGROUND ART

Glucose is the most important energy source for cell growth; therefore, a fast-growing cancer cell requires more glucose than a normal cell. One of the biochemical markers in respects to tumor malignancy is the enhanced glycolysis due to the overexpression of glucose transporters (GLUTs) and the increased activity of hexokinases (phosphorylation catalytic enzyme of hexose) in tumors [M. Zhang, Z. Zhang, D. Blessington, H. Li, T. M. Busch, V. Madrak, J. Miles, B. Chance, J. D. Glickson, G Zheng, *Bioconjugate Chem.* 2003, 14, 709-714].

The in vitro and in vivo assessment of glucose utilization has been of considerable interest to scientific communities, especially those in the biological and biomedical fields. One of the successful applications of this assessment is tumor diagnosis by positron emission tomography (PET) using a glucose probe of $^{18}$F 2-fluoro-2-deoxyglucose ($^{18}$FDG) where $^{18}$F (fluoride) is used as an isotope that emits a positron [P. Som, H. L. Atkins, D. Bandoypadhyay, J. S. Fowler, R. R. MacGregor, K. Matsui, Z. H. Oster, D. F. Sacker, C. Y. Shiue, H. Turner, C. N. Wan, A. P. Wolf, S. V. Zabinski, *J. Nud Med.* 1980, 21, 670-675; H. Yorimitsu, Y. Murakami, H. Takamatsu, S. Nishimura, E. Nakamura, *Angew. Chem. Int. Ed.* 2005, 44, 2708-2711]. PET with $^{18}$FDG is a molecular imaging modality that monitors metabolic perturbation in tumor cells and allows the imaging of the exact positions of tumors in the human body; therefore, it is widely applied in the diagnosis of various tumors [P. S. Conti, D. L. Lilien, K. Hawley, J. Keppler, S. T. Grafton, J. R. Bading, *Nucl, Med, Biol.* 1996, 23, 717-735; J. Czernin, M. E. Phelps, *Annu. Rev. Med.* 2002, 53, 89-112.].

A fluorescent 2-deoxyglucose analog, i.e., 2-[N-(7-nitrobenz-2-oxa-1,3-diazol-4-yl)amino]-2-deoxy-D-glucose (2-NBDG), was developed and extensively studied, primarily by Yoshioka et al. [K. Yoshioka, H. Takahashi, T. Homma, M. Saito, K. B. Oh, Y. Nemoto, H. Matsuoka, *Biochim. Biophys. Acta.* 1996, 1289, 5-9.]. 2-NBDG has been widely applied in various studies, especially for tumor imaging and examination of GLUT-related cell metabolism [K. Yoshioka, H. Takahashi, T. Homma, M. Saito, K. B. Oh, Y. Nemoto, H. Matsuoka, *Biochim. Biophys. Acta.* 1996, 1289, 5-9; K. Yoshioka, M. Saito, K. B. Oh, Y. Nemoto, H. Matsuoka, M. Natsume, H. Abe, *Biosci. Biotech. Biochem.* 1996, 60, 1899-1901; A. Natarajan, F. Srienc, *J. Microbiol. Methods.* 2000, 42, 87-96]. In addition, some 2-deoxyglucose analogs have been reported [Z. Cheng, J. Levi, Z. Xiong, O. Gheysens, S. Keren, X. Chen, S. S. Gambhir, *Bioconjugate Chem.* 2006, 17, 662-669; Z. Zhang, H. Li, Q. Liu, L. Zhou, M. Zhang, Q. Luo, J. Glickson, B. Chance, G Zheng, *Biosensors and Bioelectonics.* 2004, 20, 643-650; Y. Ye, S. Bloch, S. Achilefu, *J. Am. Chem. Soc,* 2004, 126, 7740-7741].

However, these analogs are all N-2-glycosylated analogs, and are disadvantageous in that a difference according to the type of α and β anomers of glucose cannot be confirmed, and that while D-glucose is an important energy source the cellular uptake of the analogs occurs only in a D-glucose-free medium, thus, it cannot be applied to a cell test in practice. Therefore, known 2-NBDG or N-2-glycosylated analogs cannot be used in the case of when the medication of an anti-cancer medicine, or obesity-related studies or diseases (e.g. diabetes) is screened.

Accordingly, the present inventors designed and synthesized novel glucose analogs in which a fluorescent dye is labeled by O-1-glycosylation unlike the known N-2-glycosylated glucose analogs.

DISCLOSURE OF INVENTION

Technical Problem

Accordingly, an object of the present invention is to provide a novel glucose analog in which a fluorescent dye is labeled by O-1-glycosylation unlike the known N-2-deoxyglucose analogs.

Another object of the present invention is to provide an asymmetric synthesis method of α and β anomers of the glucose analog.

Yet another object of the present invention is to provide a molecular bioimaging method using the glucose analog as a probe.

A further object of the present invention is to provide a screening method of curing or preventing drugs for diseases related to glucose metabolism by using the glucose analog as a probe.

Technical Solution

Hereinafter, the present invention will be described in detail.

Specifically, the glucose analog of the present invention is represented by the following Formula 1 or Formula 2:

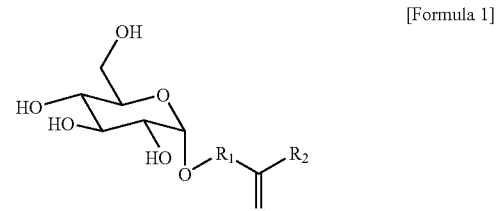
[Formula 1]

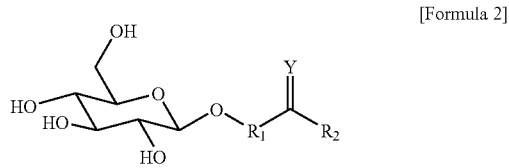
[Formula 2]

wherein $R_1$ is $-(CH_2)_n-NH-$ or $-(CH_2)_n-NH-(C_2H_4X)_m-NH-$, n is an integer in the range of 1 to 10, m is an integer in the range of 1 to 100, X is $CH_2$, O or a single bond, and when m is 2 or more each of Xs may be the same as or different from each other, $R_2$ is a fluorescent dye, and Y is O or S.

In connection with this, $R_2$ may be Cy3, Cy5, fluorescence isothiocyanate (FITC), tetramethylrhodamin isothiocyanate (RITC), Alexa, 4,4,-difluoro-4-boro-3a,4a-diaza-s-indacen (BODIPY), Texas Red or the like.

The glucose analog that is represented by Formula 1 is an α anomer, and the glucose analog that is represented by Formula 2 is an β anomer.

As more specific examples, the glucose analog is represented by the following Formula 3 or Formula 4:

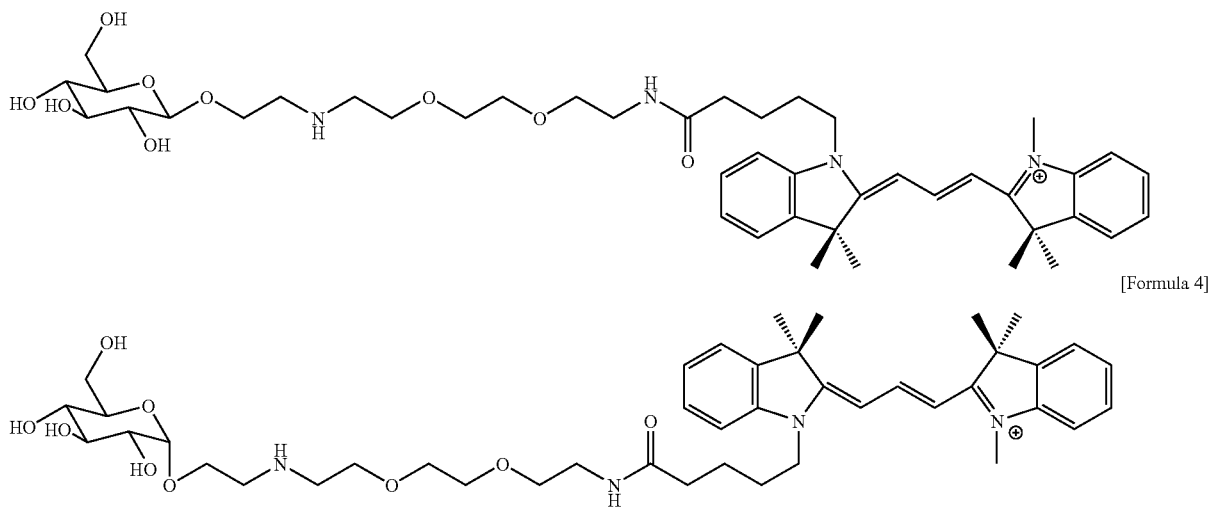

[Formula 3]

[Formula 4]

The glucose analog may be synthesized by labeling a fluorescent dye by O-1-glycosylation at the C-1 anomeric carbon position.

Specifically, the glucose analog may be synthesized by using a method that includes (a) dissolving glucose (D-glucose) in 2-bromoethanol in conjunction with an ion exchange resin and performing a reflux at a temperature in the range of 60 to 70° C. to selectively introduce 2-bromoethanol into the α and β anomeric positions;

(b) reacting the reactants obtained in step a with halogenated benzoyl in pyridine to achieve the protection by a benzoyl group, followed by separating them into the α and β anomers by using a column chromatography;

(c) reacting each of the α and β anomers that are protected by a benzoyl group obtained in step b with a diamine compound that is protected by a Boc group in an organic solvent at a temperature in the range of 40 to 50° C., followed by purification by a column chromatography; and (d) deprotecting the benzoyl group of the product obtained in step c, deprotecting the Boc groups, reacting the resulting substance with a solution containing the fluorescent dye after basification, and performing separation by using an HPLC to obtain the fluorescent dye-labeled glucose analog that is represented by Formula 1 or Formula 2.

The above synthesis method of the glucose analog may be used to simultaneously asymmetrically synthesize an α anomer that is represented by Formula 1 and a β anomer that is represented by Formula 2.

A detailed description will be given of each step of the synthesis method below.

Step a

The conformation of D-glucose is recognized to be pyranose, which is hemiacetal. Due to the special reactivity of the anomeric hydroxyl group, 2-bromoethanol can be regioselectively introduced into the anomeric position by acid-catalyzed Fischer glycosylation with a 2:1 (α:β) ratio.

Accordingly, first, after D-glucose is dissolved in 2-bromoethanol in conjunction with the ion exchange resin, the reflux is performed at a temperature in the range of 50 to 70° C., and preferably 60 to 70° C., to regioselectively introduce 2-bromoethanol into the α and β anomeric positions. In connection with this, the ratio of α and β may be obtained by using a nuclear magnetic resonance spectroscopy (NMR) [F. Fazio, M. C. Bryan, O. Blixt, J. C. Paulson, C.-H. Wong, *J. Am. Chem. Soc*, 2002, 124, 14397-14402].

Optionally, the obtained reaction mixture is filtered to remove the ion exchange resin and then concentrated in vacuo, and the glycosylated compound is purified by using a column chromatography. In connection with this, the column chromatography is a silica-gel flash column chromatography (ethyl acetate:methanol=10:1 to 5:1).

Step b

Subsequently, the reactants obtained in step a are reacted with halogenated benzoyl, preferably benzoyl chloride, in pyridine to achieve the protection by a benzoyl group and then separate them into the α and β anomers by using a column chromatography. In connection with this, the α anomer and the β anomer may be separated at the ratio of 2:1.

Preferably, after the reactants are protected by the benzoyl group and before the column chromatography is performed, the mixture was quenched with the addition of alkyl alcohol (preferably methyl alcohol) and the mixture was diluted, preferably with ethyl acetate followed by washing, drying, filtering, and condensing under reduced pressure of the organic layer.

In connection with this, a typical column chromatography may be used, and preferably the silica-gel flash column chromatography (ethyl acetate:n-hexane=1:3) is used.

Step c

Subsequently, the α and β anomers that are protected by using the benzoyl group obtained in step b are reacted with compounds containing Boc groups in an organic solvent at a temperature in the range of 40 to 60° C., and preferably 40 to 50° C., and then perform purification by using a column chromatography.

In connection with this, it is preferable that before purifying the reactants the solution obtained is diluted (preferably, ddH$_2$O is used), extracted (preferably, ethyl acetate is used), washed (preferably, brine is used), and condensed under reduced pressure according to a typical method.

A typical organic solvent may be used as the above organic solvent. Preferably, the solvent is dimethyl formamide (DMF) and triethyl amine (TEA). The compound containing the Boc group includes an amine connection group and the Boc groups, and preferably N-Boc-3,6-dioxaoctane-1,8-diamine having the amine connection group. However, the compound is not limited thereto.

In connection with this, a typical column chromatography may be used, and preferably the silica-gel flash column chromatography (chloroform:ethanol TEA=87:8:5) is used.

Step d

Finally, the benzoyl group of the product obtained in step c is deprotected, the Boc groups are deprotected, the resulting substance is reacted with a solution containing the fluorescent dye after basification, and separation by using an HPLC is performed to obtain the fluorescent dye-labeled glucose analog that is represented by Formula 1 or Formula 2.

For the debenzoylation, preferably, sodium methoxide may be added to the methyl alcohol (MeOH) solution in which the product obtained in step c is dissolved to achieve the reaction, thereby performing the deprotection.

For the deprotection of the Boc groups may be performed by adding a dichloromethane solution containing a 50% trifluoroacetic acid (TFA) to the compound in which the benzoyl group is deprotected and conducting $N_2$ purging to perform concentration.

Meanwhile, in order to remove the trifluoroacetic acid that remains on the reaction mixture after being used to deprotect the Boc groups, the basification is performed. The basification may be performed by reacting a dimethylformamide (DMF) solution in which the deprotected compound is dissolved with diisopropylethylamine (DIPEA). Through the basification treatment, chiral glucoside having primary amine is obtained.

In the present invention, the fluorescent dye may be Cy3, Cy5, fluorescence isothiocyanate (FITC), tetramethylrhodamin isothiocyanate (RITC), Alexa, 4,4,-difluoro-4-boro-3a,4a-diaza-s-indacen (BODIPY), Texas Red or the like. Preferably Cy3 is used because it is stable in respects to a light source having the high intensity such as a beam, a laser or the like and is extensively used various types of bioassay systems. Therefore, the solution containing the fluorescent dye is preferably the dimethylformamide (DMF) solution that contains Cy3-COOH and the reaction agent, 1-(3-dimethylaminopropyl)-3-ethylcarbodiimide (EDC).

However, the organic compound such as biotin, the inorganic compound such as nanoparticles or the like may be used according to the usage.

Cy3 is labeled at the anomeric position of glucoside through the amide bonding by EDC, and separated by using HPLC to obtain the fluorescent dye-labeled glucose analog (a anomer and β anomer) according to the present invention. The final products may be completely characterized by $^1H$, $^{13}C$ NMR, MALDI-TOF mass spectrometry, the high resolution mass spectrometry or the like.

The glucose analog that is obtained by using the synthesis method according to the present invention acts as the analog of D-glucose, thus, it selectively enters into cancer cells, for example, cells such as lung cancer cells having enhanced glucose-metabolism. The intracellular uptake of the glucose analog with or without the presence of various types of concentrations of D-glucose is performed according to a time- and dose-depending manner. On the other hand, the uptake of the glucose analog is not affected by L-glucose and the osmotic pressure in the medium. This means that the glucose analog according to the present invention is transported into cells due to the glucose-specific transport system.

Among them, the α glucose anomer that is represented by Formula 1 shower a higher performance as a glucose uptake probe as compared to the known compound of the following Formula 5, that is, 2-NBDG that is obtained by labeling NBD that is the fluorescent dye by using N-2-glycosylation.

[Formula 5]

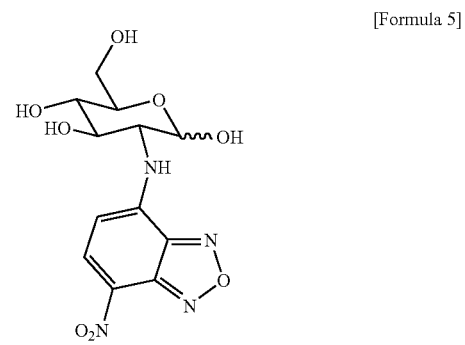 [SMILES: O=[N+]([O-])c1ccc(NC2C(O)OC(CO)C(O)C2O)c2nonc12]

That is, 2-NBDG that is a known fluorescent glucose analog is hardly detected at a concentration of 125 μM, but the glucose analog is detected at a low concentration of even 12.5 μM. Therefore, the glucose analog provided by the present invention may act as a bioprobe and be efficiently applied to bioimaging, molecular bioimaging, bioassay, novel medicine screening or the like.

In particular, the glucose analog according to the present invention may be applied to the molecular bioimaging method for cancer or tumor imaging or examination of glucose transporters-related cell metabolism.

In connection with this, in the molecular bioimaging method, examples of a measuring device include, but are not limited to a confocal laser scanning microscope (CLSM), an inverted fluorescent microscope, a fluorescent activated cell sorter (FACS), a microplate reader, a high content screening or the like.

In addition, the analog may be used at a concentration in the range of 1 to 100 μM, preferably 10 to 20 μM, and most preferably 12.5 μM, and an incubation time may be 35 min or less and preferably 25 to 35 min.

Meanwhile, the present invention provides a screening method of curing or preventing drugs for diseases regarding glucose metabolism using a glucose analog as a bioprobe.

As described above, the glucose metabolism is the most important metabolism, and if there is a problem in this metabolism, various types of diseases occurs. Examples of the diseases may include a cancer or a tumor, and the glucose analog according to the present invention may be applied to the screening method for detecting anticancers.

Illustrative but non-limiting examples of the anticancers may preferably include curing or preventing agents for lung cancer, stomach cancer, liver cancer, or colon cancer.

The glucose analog according to the present invention has a high probability as a novel bioprobe used to screen an efficient novel biomedicines used to cure diseases directly related to the glucose metabolism, that is, diabetes which is caused by the inefficient glucose metabolism and/or uptake in cells, and obesity which is caused by the excessively active glucose metabolism.

Therefore, the analog according to the present invention may be used to evaluate performance of physiological activity controlling substances and novel medicines by using a novel screening method, and to screen the novel medicines.

Advantageous Effects

The glucose analog according to the present invention has excellent performance as a glucose uptake probe as compared to known 2-NBDG and a novel material that can monitor the uptake of glucose in a normal medium state unlike the 2-NBDG or N-2-glycosylated analog, therefore, the glucose analog can be applied to molecular bioimaging, bioassay, and screening of curing or preventing drugs for diseases regarding glucose metabolism.

BRIEF DESCRIPTION OF THE DRAWINGS

The above and other features and advantages of the present invention will become more apparent by describing in detail preferred embodiments thereof with reference to the attached drawings in which:

FIG. 14A is a graph that illustrates the Cy3-Glc-α uptake by A549 cells, and the fluorescence intensities are expressed as arbitrary unit (a.u.) determined by continuous measurement from ROIs (Regions of Interest) in five independent cells marked on B based on unbiased selection. FIG. 14B illustrates merged phase-contrast image and fluorescence images in A549 cells captured by live-cell imaging with a confocal laser scanning microscope (CLSM), in which (a) illustrates A549 cells immediately after the Cy3-Glc-α treatment, and (b) illustrates A549 cells after 60 min after the Cy3-Glc-α treatment (Scale bar=20 μm).

MODE FOR INVENTION

Figure 1:
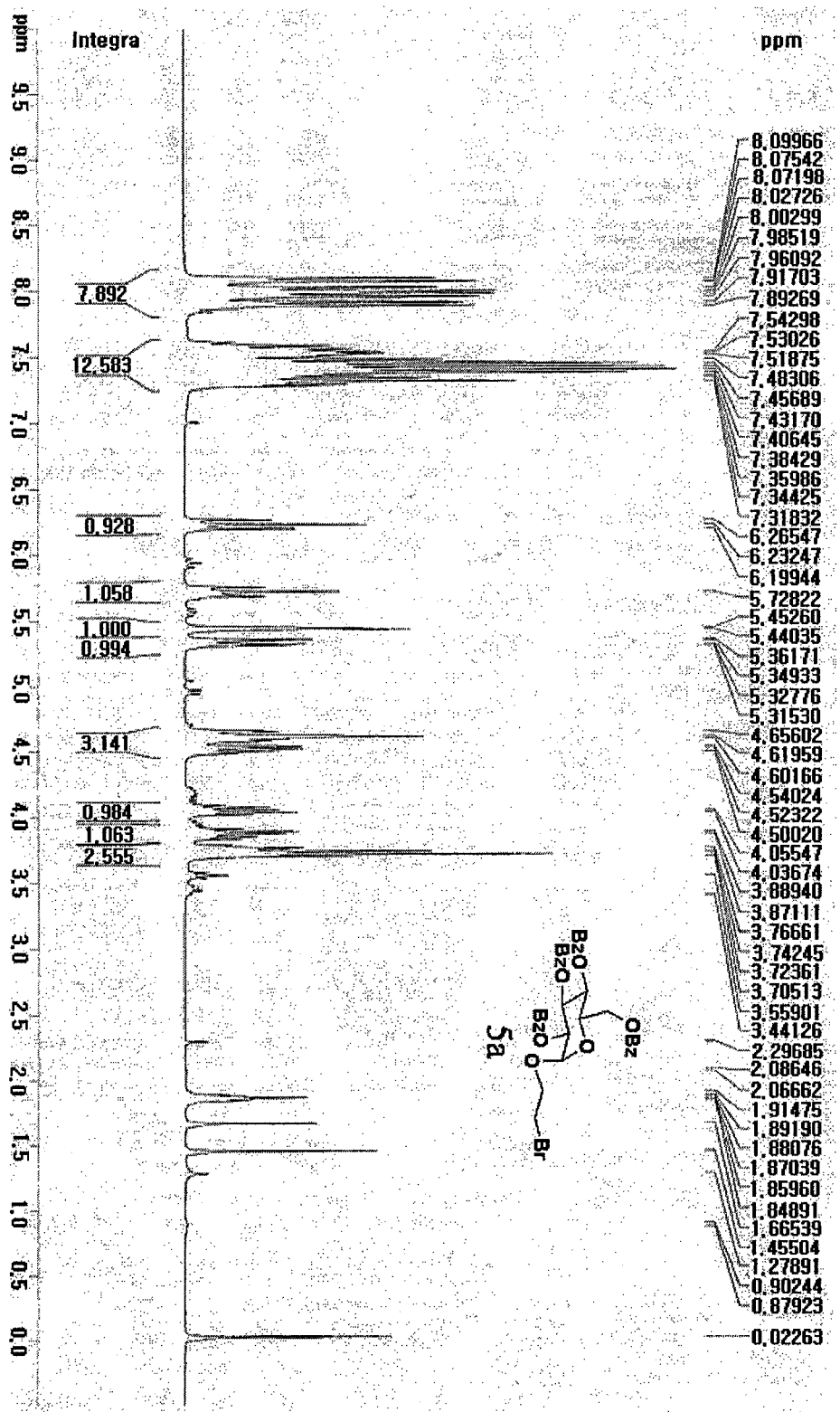
FIG. 1 illustrates $^1$H NMR data of a (2-bromoethyl)-2,3,4,6-tetra-O-benzoyl-α-D-glucoside (5a) compound that is an intermediate obtained in Example 1.
Figure 2:
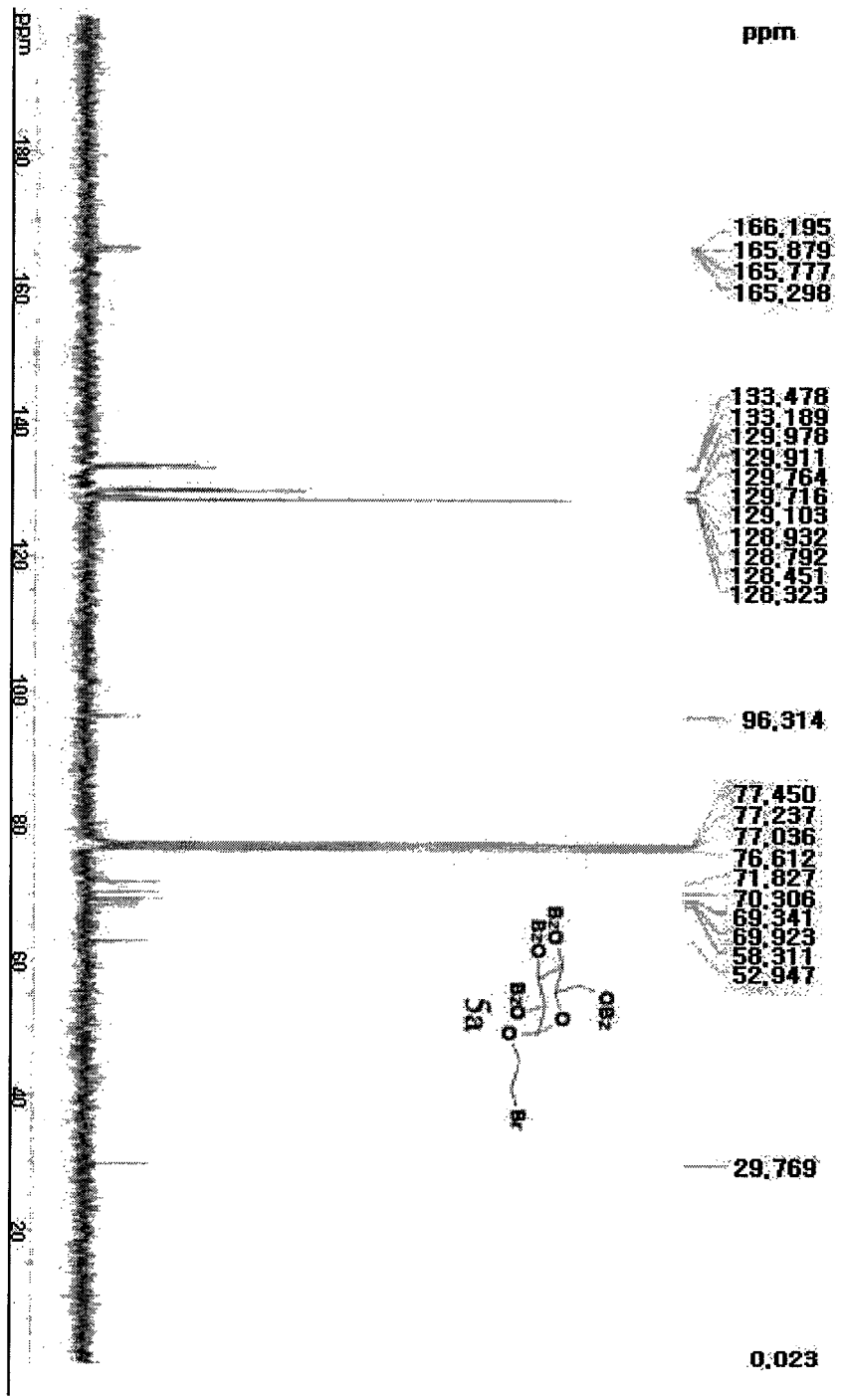
FIG. 2 illustrates $^{13}$C NMR data of a (2-bromoethyl)-2,3,4,6-tetra-O-benzoyl-α-D-glucoside (5a) compound that is an intermediate obtained in Example 1.
Figure 3:
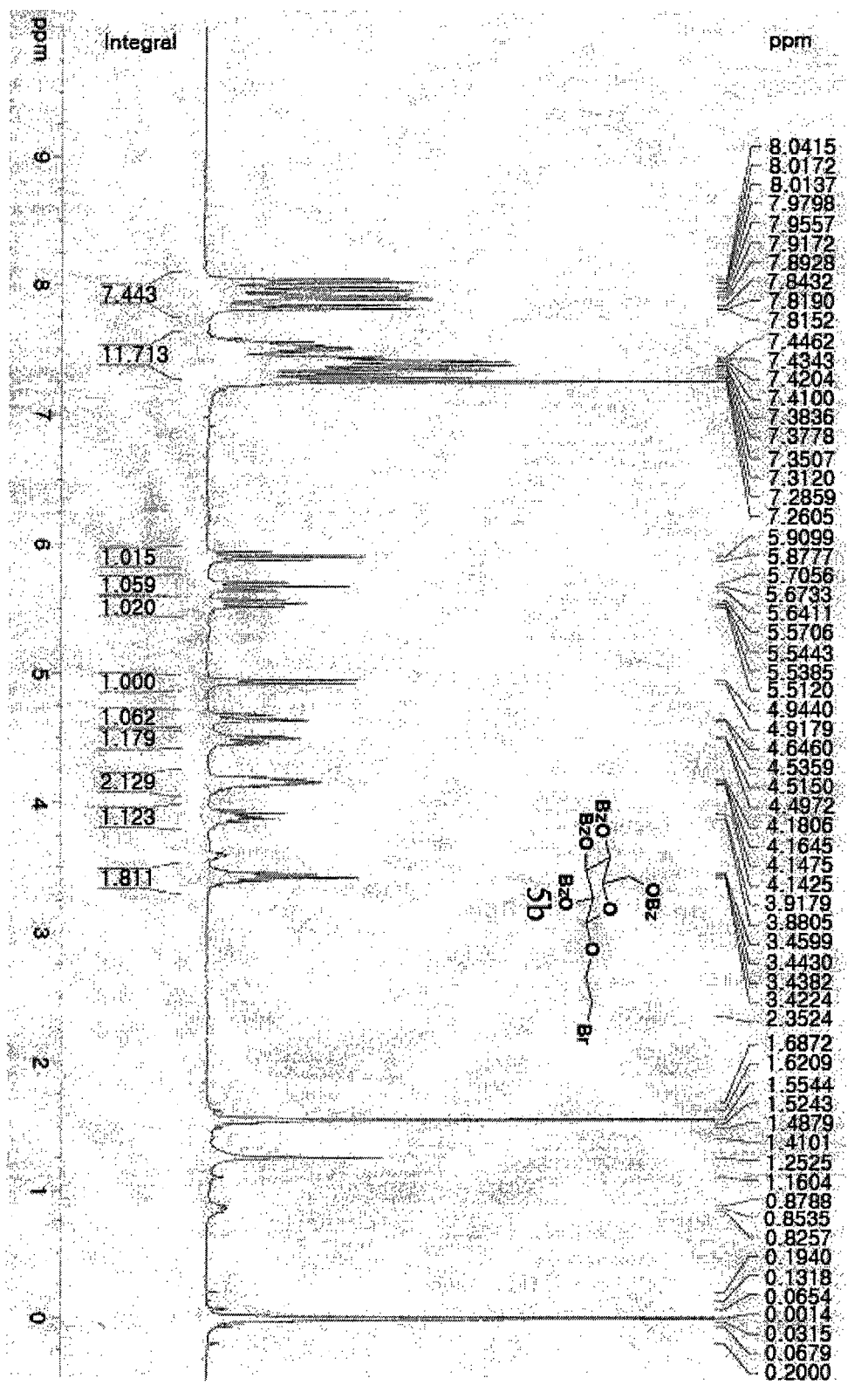
FIG. 3 illustrates $^1$H NMR data of a (2-bromoethyl)-2,3,4,6-tetra-O-benzoyl-β-D-glucoside (5b) compound that is an intermediate obtained in Example 1.
Figure 4:
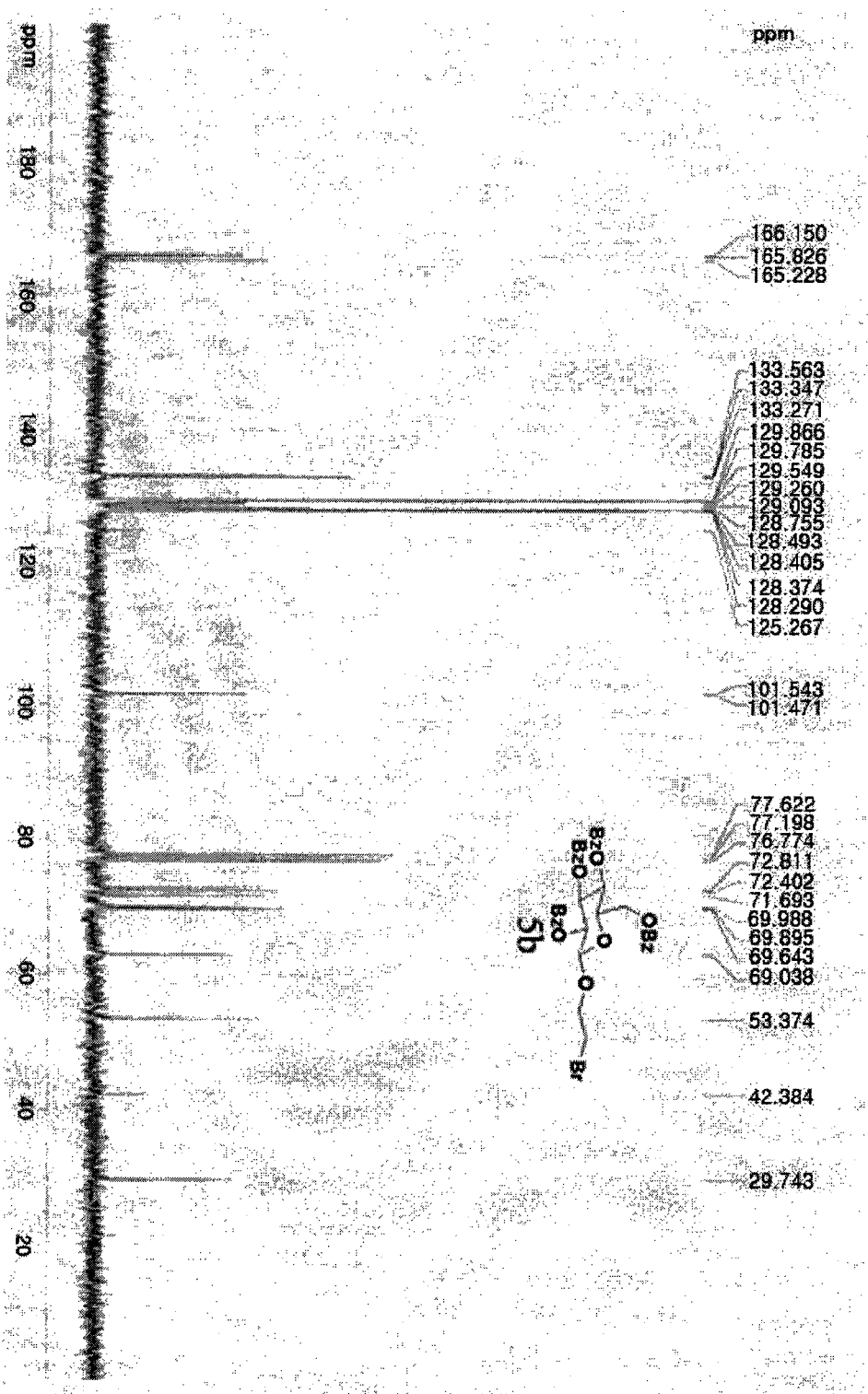
FIG. 4 illustrates $^{13}$C NMR data of a (2-bromoethyl)-2,3,4,6-tetra-O-benzoyl-β-D-glucoside (5b) compound that is an intermediate obtained in Example 1.
Figure 5:
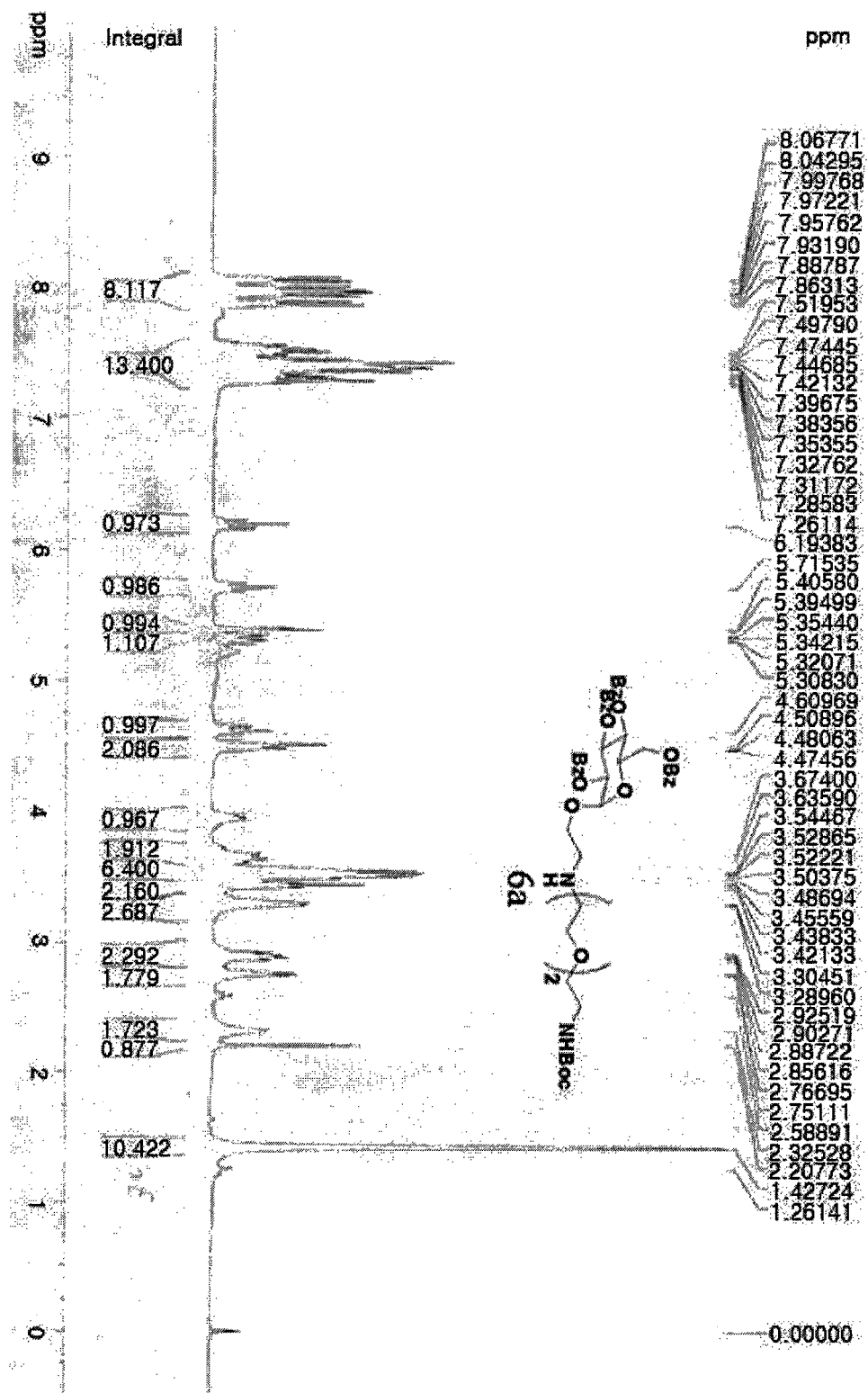
FIG. 5 illustrates $^1$H NMR data of a 2-(N-boc-3,6-dioxaoctane-1,8-diaminoethyl)]-2,3,4,6-tetra-O-benzoyl-α-D-glucoside (6a) compound that is an intermediate obtained in Example 1.
Figure 6:
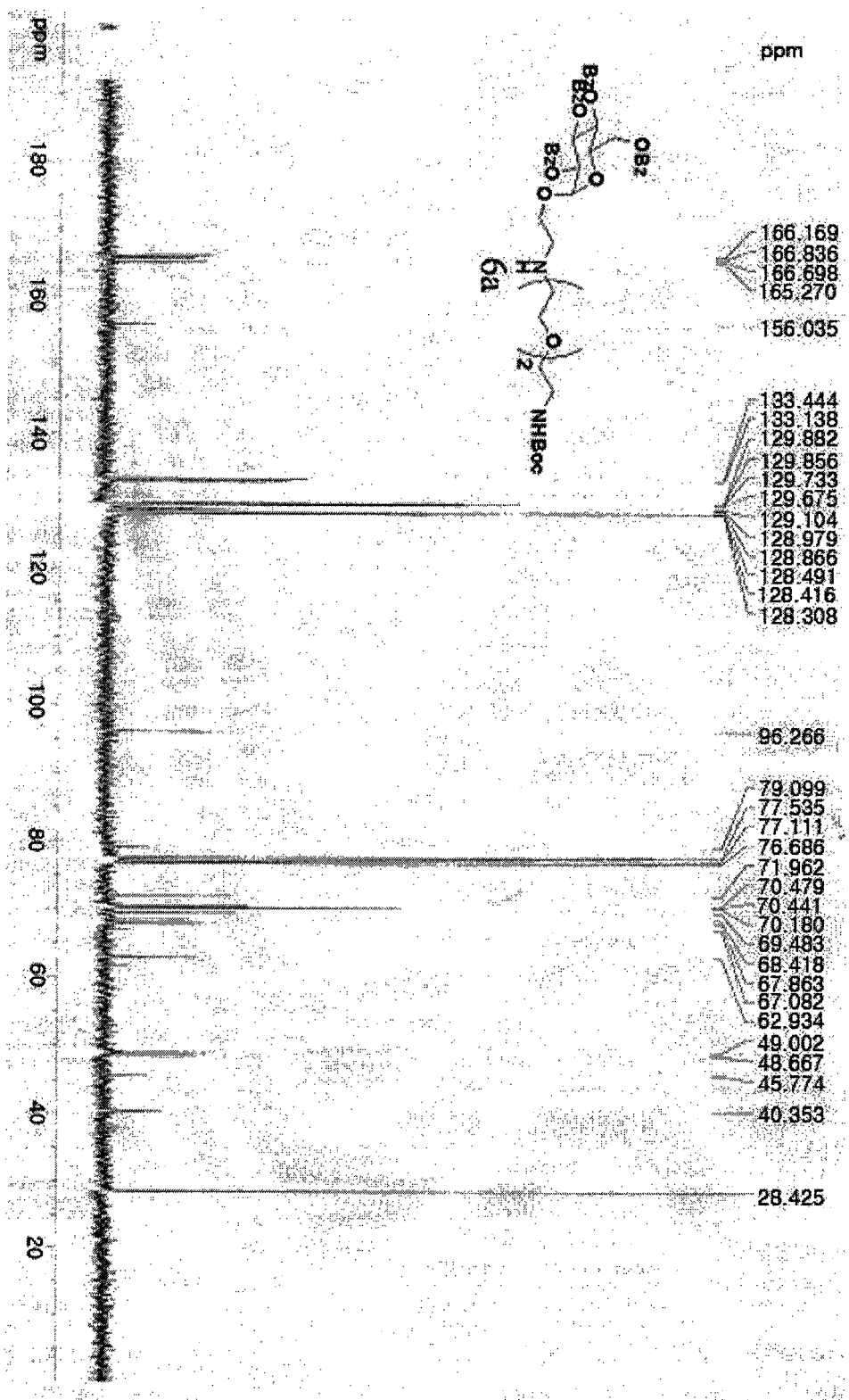
FIG. 6 illustrates $^{13}$C NMR data of a 2-(N-boc-3,6-dioxaoctane-1,8-diaminoethyl)]-2,3,4,6-tetra-O-benzoyl-α-D-glucoside (6a) compound that is an intermediate obtained in Example 1.
Figure 7:
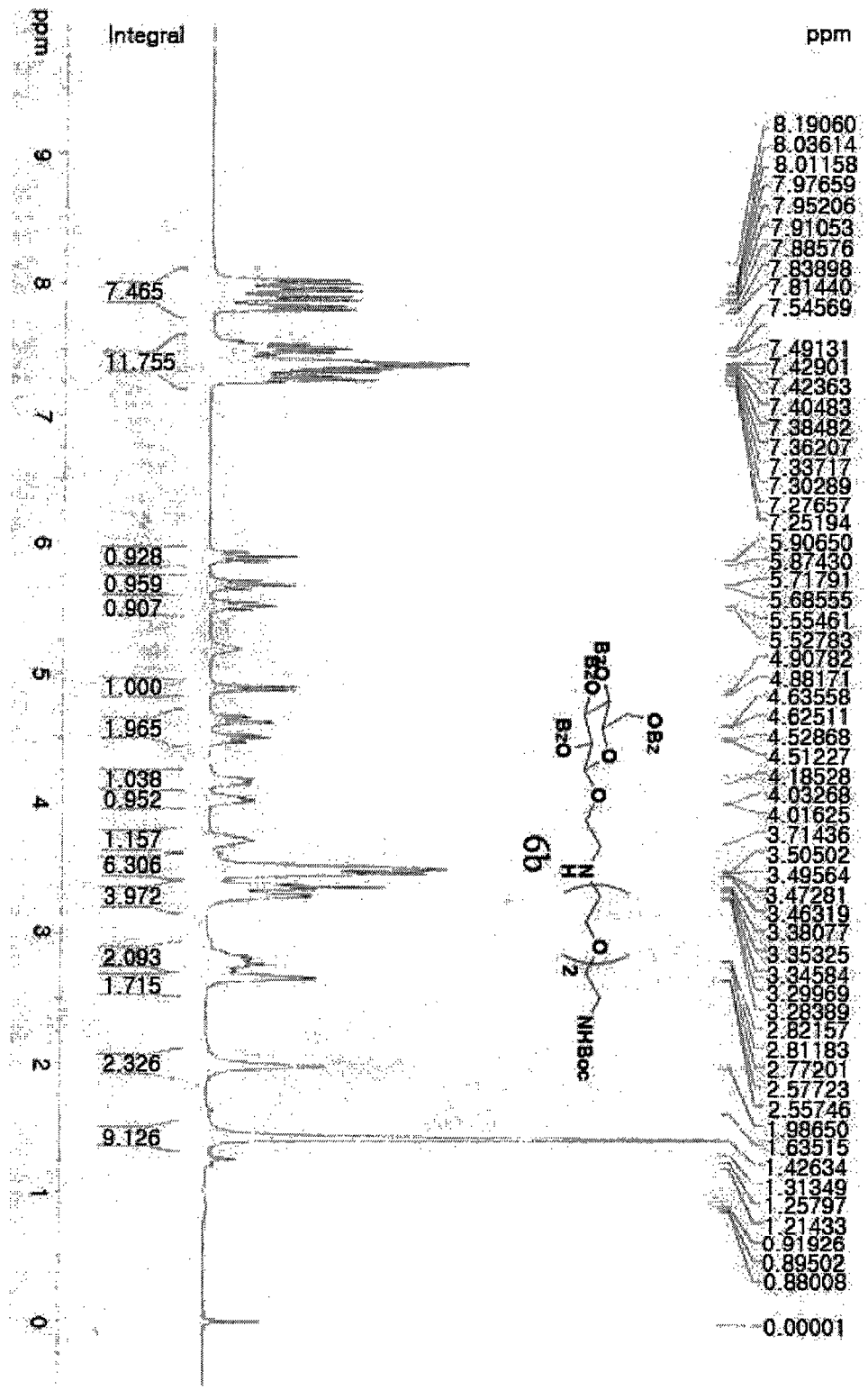
FIG. 7 illustrates $^1$H NMR data of a 2-(N-boc-3,6-dioxaoctane-1,8-diaminoethyl)]-2,3,4,6-tetra-O-benzoyl-β-D-glucoside (6b) compound that is an intermediate obtained in Example 1.
Figure 8:
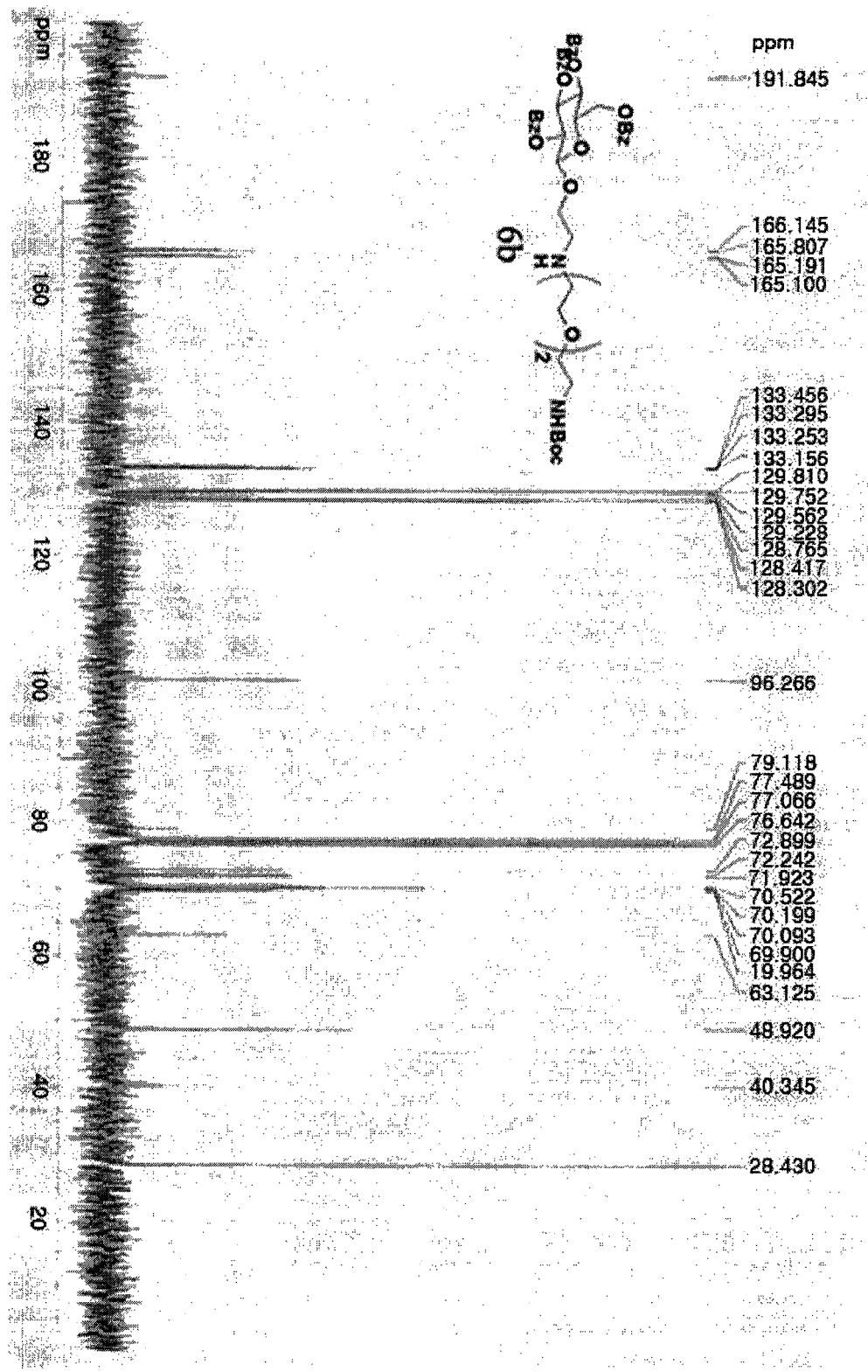
FIG. 8 illustrates $^{13}$C NMR data of a 2-(N-boc-3,6-dioxaoctane-1,8-diaminoethyl)]-2,3,4,6-tetra-O-benzoyl-β-D-glucoside (6b) compound that is an intermediate obtained in Example 1.
Figure 9:
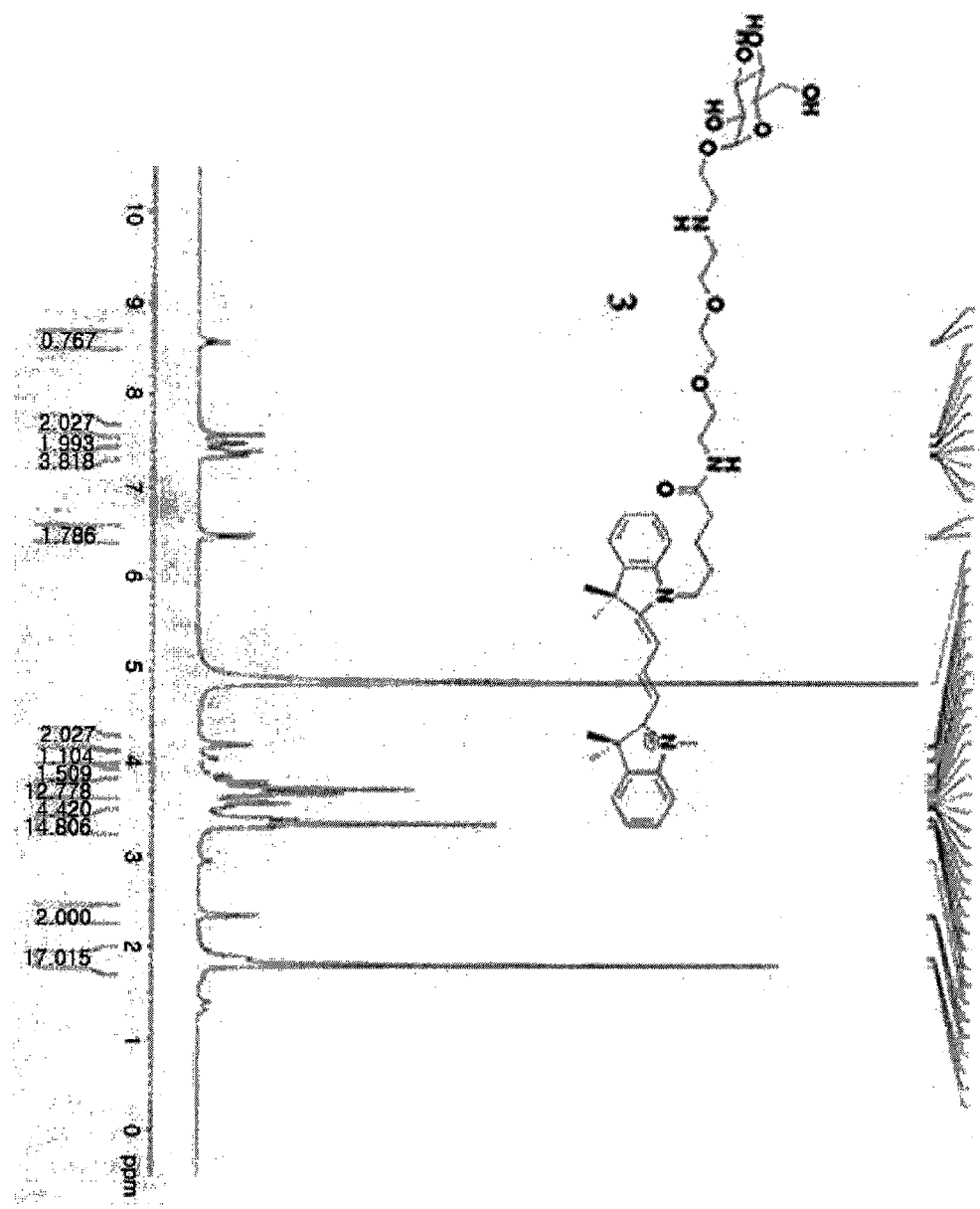
FIG. 9 illustrates $^1$H NMR data of [2-(N-Cy3-3,6-dioxaoctane-1,8-diaminoethyl)]-α-D-glucose (3) that is a final product obtained in Example 1.
Figure 10:
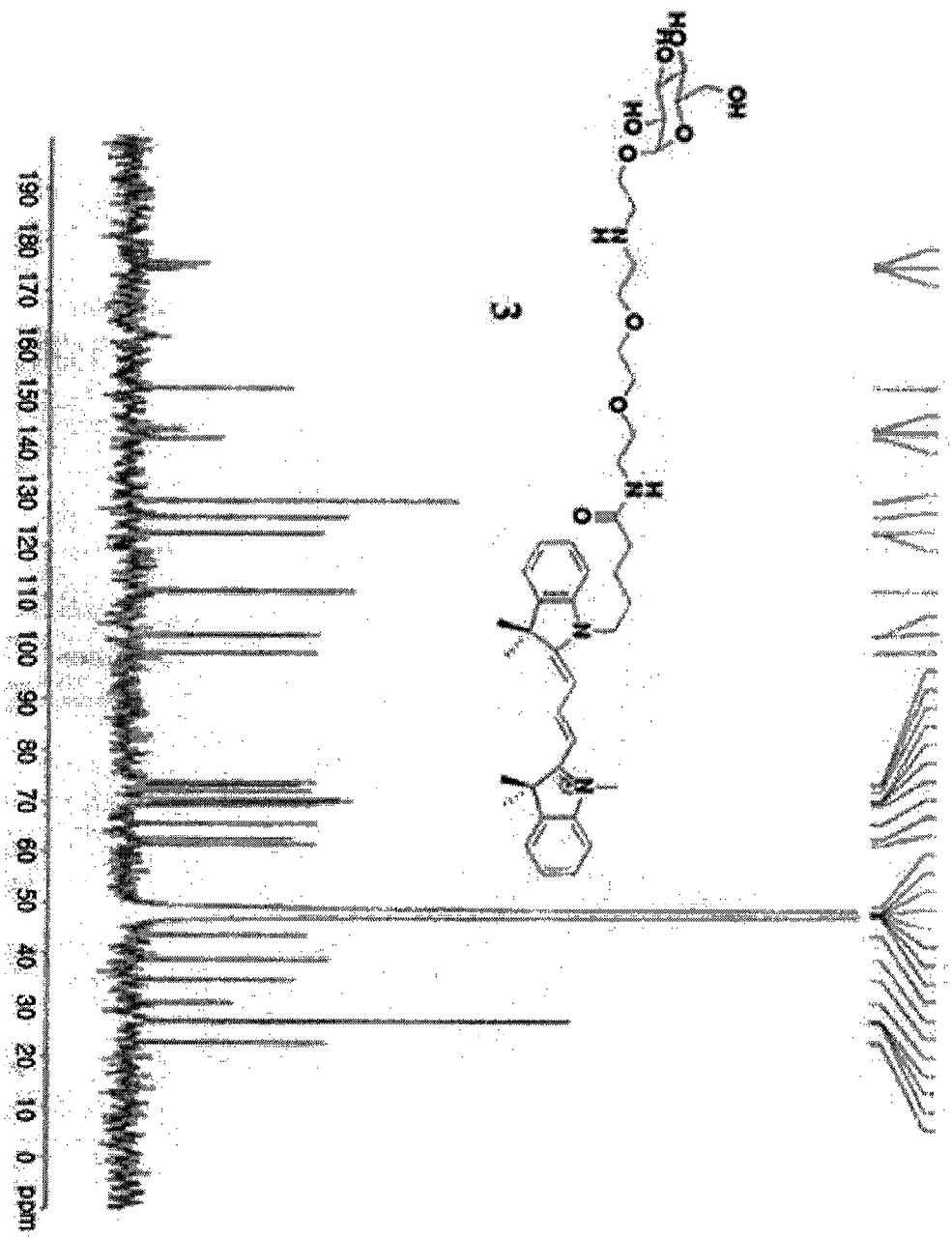
FIG. 10 illustrates $^{13}$C NMR data of [2-(N-Cy3-3,6-dioxaoctane-1,8-diaminoethyl)]-α-D-glucose (3) that is a final product obtained in Example 1.
Figure 11:
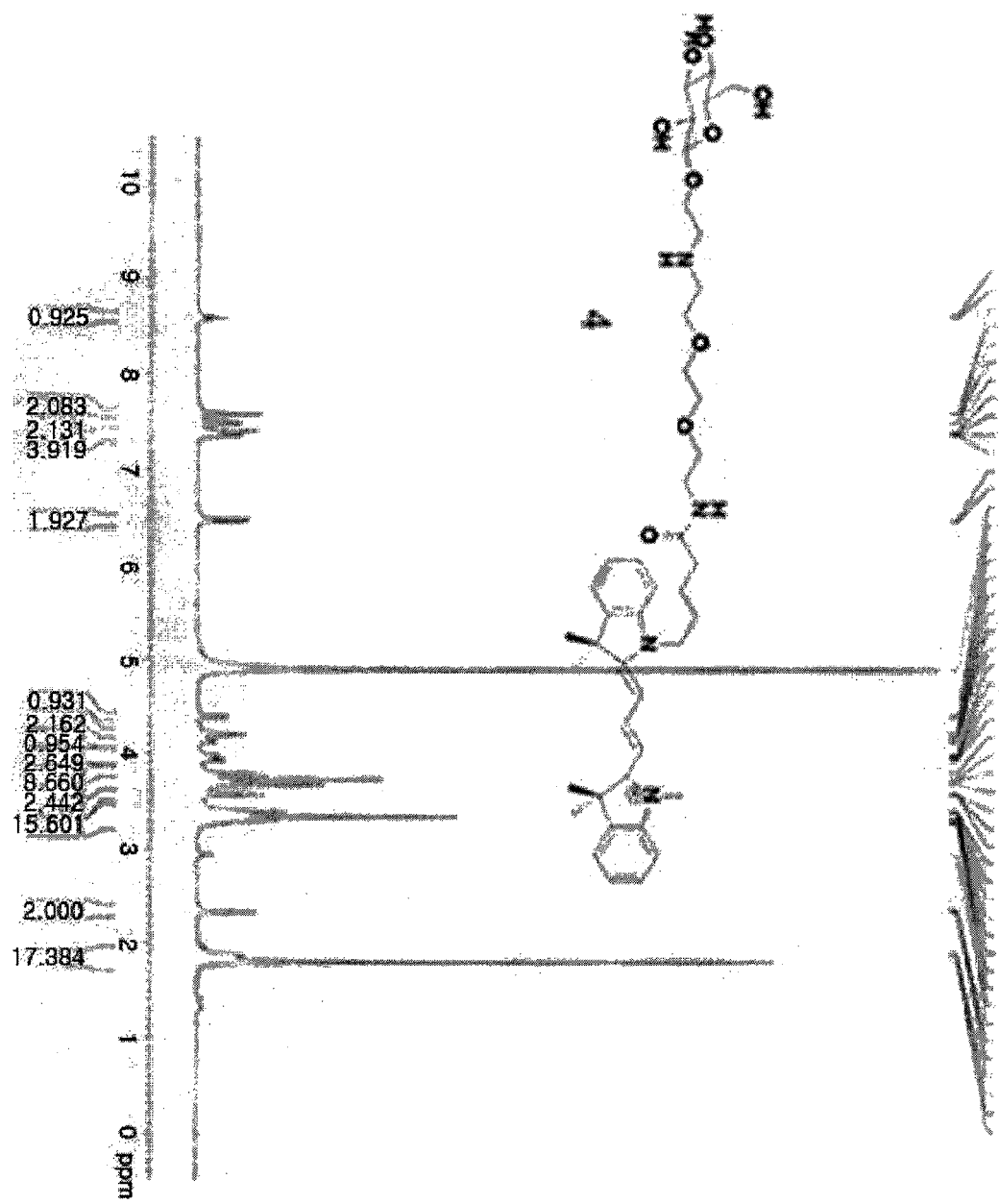
FIG. 11 illustrates $^1$H NMR data of [2-(N-Cy3-3,6-dioxaoctane-1,8-diaminoethyl)]-β-D-glucose (4) that is a final product obtained in Example 1.
Figure 12:
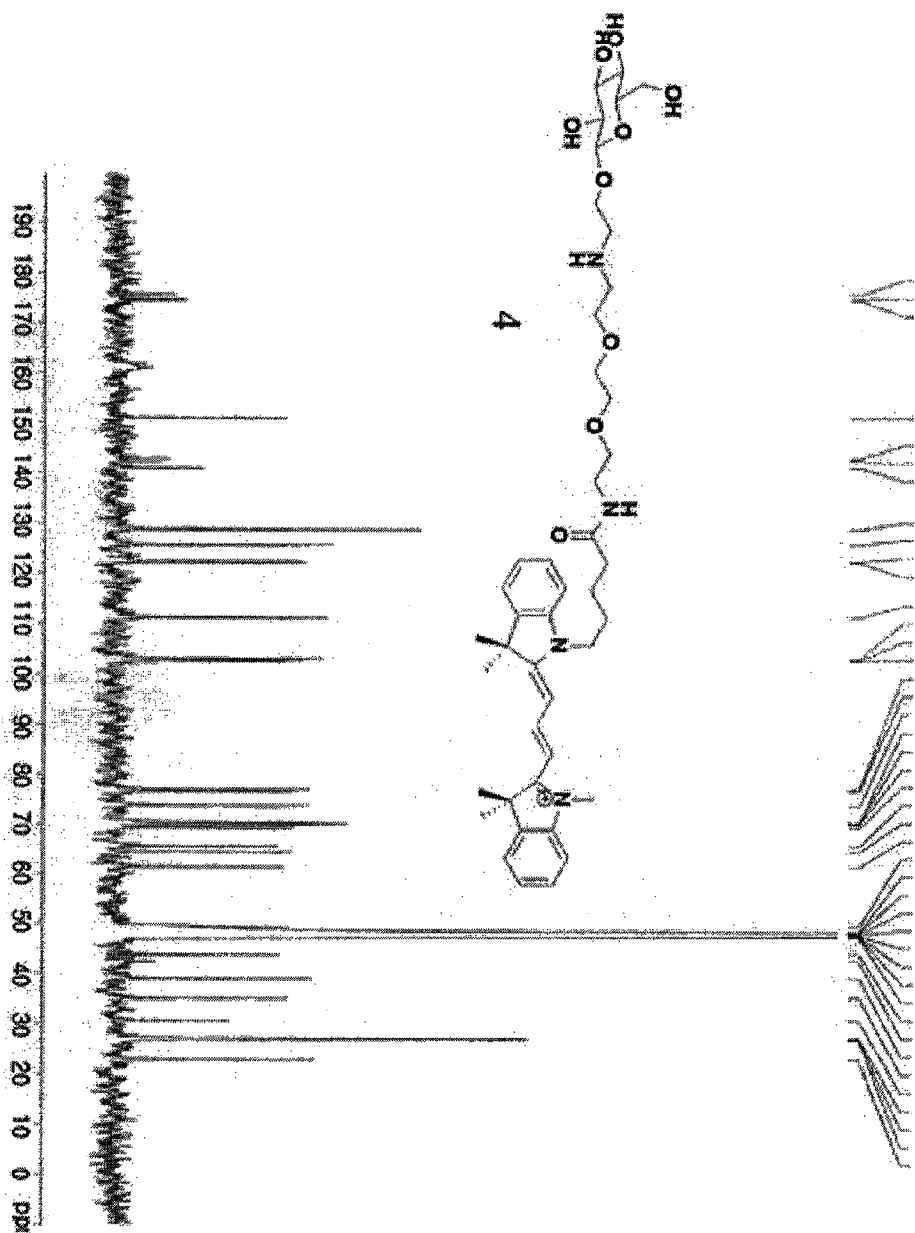
FIG. 12 illustrates $^{13}$C NMR data of [2-(N-Cy3-3,6-dioxaoctane-1,8-diaminoethyl)]-β-D-glucose (4) that is a final product obtained in Example 1.

A better understanding of the present invention may be obtained in light of the following Examples which are set forth to illustrate, but are not to be construed to limit the present invention.

EXAMPLE 1

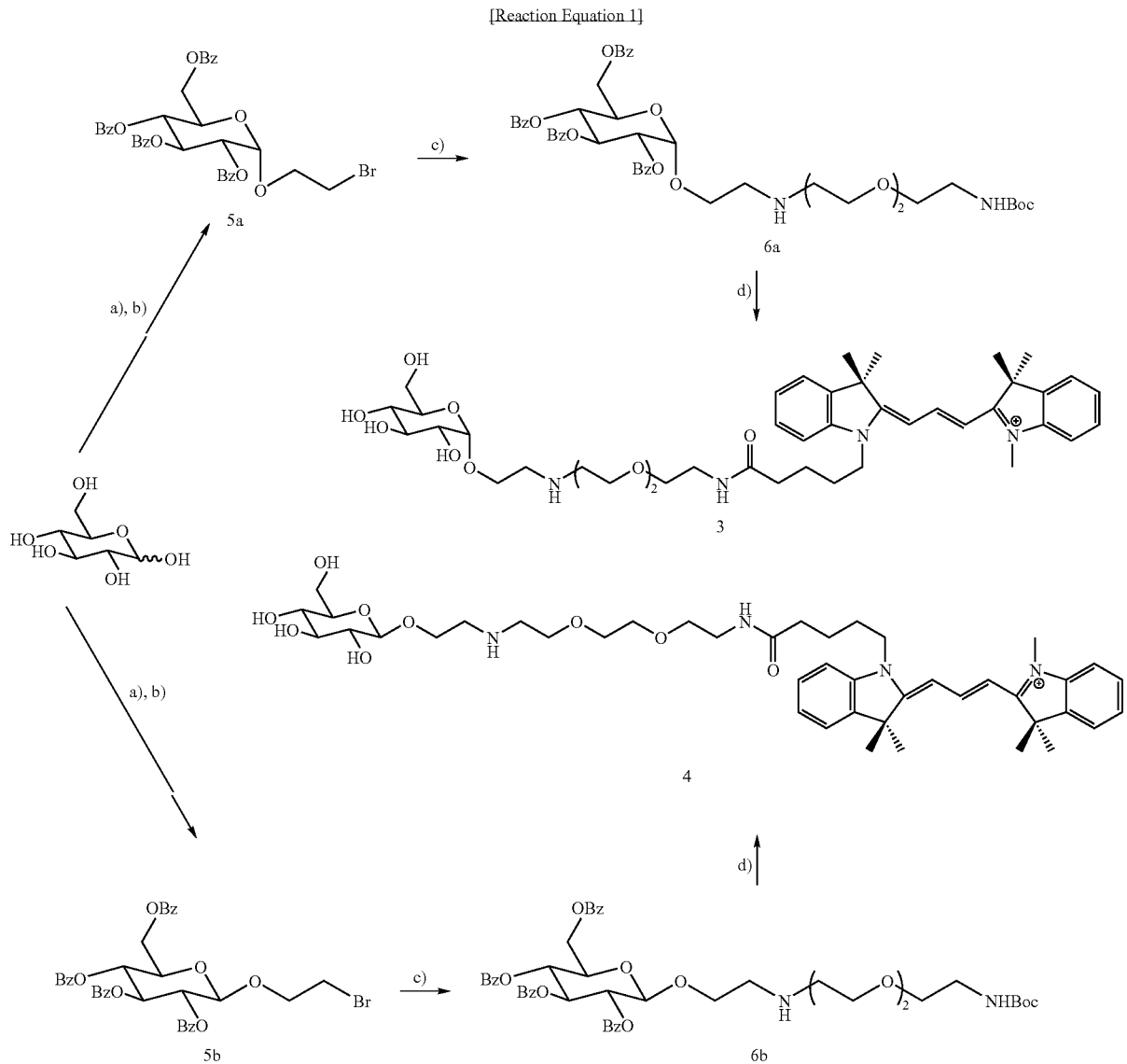

[Reaction Equation 1]

a) 2-bromoethanol, the Dowex 50WX8-400 ion exchange resin, 70° C. reflux; b) benzoyl chloride, pyridine, dimethyl aminopyridine (DMAP); c) N-Boc-3,6-dioxaoctane-1,8-diamine, triethylamine, dimethylformamide (DMF), 50° C.; d) (i) sodium methoxide (NaOMe), methanol; (ii) the 50% trifluoroacetic acid (TFA)/dichloromethane (DCM); (iii) Cy3-COOH, EDC, diisopropylethylamine (DIPEA), dimethylformamide (DMF)

1. Preparation of (2-bromoethyl)-2,3,4,6-tetra-O-benzoyl-α-D-glucoside (5a) and (2-bromoethyl)-2,3,4,6-tetra-O-benzoyl-β-D-glucoside (5b)

Glucose (1 g, 5.55 mmol) was dissolved in 2-bromoethanol (6 mL, 85 mmol) with Dowex 50WX8-400 ion exchange resin. The reaction mixture was refluxed at 70° C. overnight and the reaction completion was monitored by TLC [F. Fazio, M. C. Bryan, O. Blixt, J. C. Paulson, C.-H. Wong, *J. Am. Chem. Soc*, 2002, 124, 14397-14402]. Subsequently, the reaction mixture was filtered to remove the resin and concentrated in vacuo. After the purification of glycosylated compound by silica-gel flash column chromatography (ethyl acetate:methanol=10:1 to 5:1), the desired compound was achieved as a mixture of α and β anomers in 2:1 ratio (total yield 74%) confirmed by nuclear magnetic resonance (NMR). The free hydroxyl groups on the resulting (2-bromoethyl)-D-glucoside (2.7 g, 9.5 mmol) were benzoylated in pyridine (60 mL) by drop-wise addition of benzoyl chloride (8.8 mL, 76 mmol) over 10 min at 0° C., followed by stirring at room temperature for overnight in the presence of dimethylaminopyridine (DMAP) (116 mg, 0.952 mmol) [a] M. A. Maier, C. G Yannopoulos, N. Mohamed, A. Roland, H. Fritz, V. Mohan, G. Just, M. Manoharan, *Bioconjugate Chem.* 2003, 14, 1829; b) R. E. Campbell, M. E. Tanner, *J. Org. Chem.* 1999, 64, 9487-9492]. The mixture was quenched with the addition of methanol (10 mL) and the reaction mixture was diluted with ethyl acetate. The organic layer was washed with the 1N hydrochloric acid (HCl) and sat sodium bicarbonate (NaHCO$_3$), and dried over anhydrous magnesium sulfate (MgSO$_4$). Then, organic layer was filtered and condensed under reduced pressure, and the desired each anomer was successively isolated by silica-gel flash column chromatography (ethyl acetate:n-hexane=1:3) in a 2:1 ($\alpha$:$\beta$) ratio.

(1) $\alpha$[(2-bromoethyl)-2,3,4,6-tetra-O-benzoyl-$\alpha$-D-glucoside (5a)]: $^1$H NMR (300 MHz, CDCl$_3$) $\delta$8.097.89 (m, 8H), 7.547.31 (m, 12H), 6.23 (t, J=9.9 Hz, 1H), 5.70 (t, J=9.9 Hz, 1H), 5.44 (d, J=3.6 Hz, 1H), 5.33 (dd, J=10.1, 3.7 Hz, 1H), 4.644.56 (m, 2H), 4.48 (dd, J=11.9, 5.1 Hz, 1H), 4.164.03 (m, 1H), 3.943.85 (m, 1H), 3.763.70 (m, 2H); $^{13}$C NMR (75 MHz, CDCl$_3$) $\delta$166.20, 165.88, 165.78, 165.30, 133.48, 133.19, 129.98, 129.91, 129.76, 129.72, 129.63, 129.10, 128.93, 128.79, 128.45, 128.32, 96.31, 71.83, 70.30, 69.34, 68.92, 68.31, 62.95, 29.80; MALDI TOF MS calcd for C$_{36}$H$_{43}$O$_{12}$ [M+H]$^+$: 703.11; found: 703.05.

(2) $\beta$(2-bromoethyl)-2,3,4,6-tetra-O-benzoyl-$\beta$-D-glucoside (5b)]: $^1$H NMR (300 MHz, CDCl$_3$) $\delta$8.047.81 (m, 8H), 7.447.28 (m, 12H), 5.91 (t, J=9.6 Hz, 1H), 5.67 (t, J=9.7 Hz, 1H), 5.54 (dd, J=7.9, 1.7 Hz, 1H), 4.93 (d, J=7.8 Hz, 1H), 4.66 (dd, J=9.1, 3.0 Hz, 1H), 4.48 (dd, J=6.8, 5.3 Hz, 1H), 4.24-4.07 (m, 2H), 3.94-3.83 (m, 1H), 3.49-3.36 (m, 2H); $^{13}$C NMR (75 MHz, CDCl$_3$) $\delta$166.15, 165.82, 165.22, 133.56, 133.34, 129.86, 129.78, 129.55, 129.26, 129.09, 128.75, 128.49, 128.40, 128.37, 128.29, 101.54, 72.81, 72.40, 71.69, 69.89, 69.64, 63.03, 29.74; MALDI TOF MS calcd for C$_{36}$H$_{43}$O$_{12}$ [M+H]$^+$: 703.11; found: 703.16.

Meanwhile, $^1$H NMR and $^{13}$C NMR data of the compounds 5a and 5b are shown in FIGS. 1 to 4.

2. Preparation of 2-(N-boc-3,6-dioxaoctane-1,8-diaminoethyl)]-2,3,4,6-tetra-O-benzoyl-$\alpha$-D-glucoside (6a) and 2-(N-boc-3,6-dioxaoctane-1,8-diaminoethyl)]-2,3,4,6-tetra-O-benzoyl-$\beta$-D-glucoside (6b)

(1) 2-(N-boc-3,6-dioxaoctane-1,8-diaminoethyl)]-2,3,4,6-tetra-O-benzoyl-$\alpha$-D-glucoside (6a)

To a solution of compound 5a (120 mg, 0.170 mmol) in 1 mL anhydrous DMF were added N-Boc-3,6-dioxaoctane-1,8-diamine [a) M. Trester-Zedlitz, K. Kamada, S. K. Burley, D. Fenyo, B. T. Chait, T. W. Muir, *J. Am. Chem. Soc.* 2003, 125, 2416-2425; b) Y Li, Y.-M. Zhu, H.-J. Jiang, J.-P. Pan, G-S. Wu, J.-M. Wu, Y.-L. Shi, J.-D. Yang, B.-A. Wu, *J. Med. Chem.* 2000, 43, 1635-1640] (127 mg, 0.512 mmol) and TEA (71 µL, 0.512 mmol), and the reaction mixture was stirred at 50° C. After the reaction completion was monitored by TLC, the resulting solution was diluted with ddH$_2$O, and then extracted with ethyl acetate. The combined organic layer was washed with brine, condensed under reduced pressure, and purified by silica-gel flash column chromatography (chloroform:ethanol:TEA=87:8:5) to obtain compound 6a as yellowish oily compound (114 mg, 76%).

$^1$H NMR (300 MHz, CDCl$_3$) $\delta$8067.86 (m, 8H), 7.527.28 (m, 12H), 6.19 (t, J=9.8 Hz, 1H), 5.71 (t, J=9.6 Hz, 1H), 5.40 (d, J=3.5 Hz, 1H), 5.33 (dd, J=10.1, 3.7 Hz, 1H), 4.62 (d, J=9.5 Hz, 1H), 4.504.47 (m, 2H), 3.993.94 (m, 1H), 3.723.60 (m, 2H), 3.543.50 (m, 6H), 3.44 (t, J=5.1 Hz, 2H), 3.29 (d, J=4.5 Hz, 2H), 2.922.86 (m, 2H), 2.782.73 (m, 2H), 2.32 (s, 2H), 2.20 (s, 1H), 1.42 (s, 9H); $^{13}$C NMR (75 MHz, CDCl$_3$) $\delta$166.17, 165.83, 165.69, 165.27, 156.03, 133.44, 133.13, 129.88, 129.85, 129.73, 129.67, 129.10, 128.97, 128.86, 128.49, 128.41, 128.30, 96.26, 79.09, 71.96, 70.47, 70.44, 70.18, 69.48, 68.41, 67.86, 67.08, 62.93, 49.00, 48.66, 40.35, 28.42; MALDI TOF MS calcd for C$_{47}$H$_{55}$N$_2$O$_{14}$ [M+H]$^+$: 871.36; found: 871.51

(2) 2-(N-boc-3,6-dioxaoctane-1,8-diaminoethyl)]-2,3,4,6-tetra-O-benzoyl-$\beta$-D-glucoside (6b)

The same procedure, except using compound 5b instead of compound 5a, was performed to obtain compound 6b (104 mg, 70%).

$^1$H NMR (300 MHz, CDCl$_3$) $\delta$8.197.81 (m, 8H), 7.547.25 (m, 12H), 5.90 (t, J=9.6 Hz, 1H), 5.68 (t, J=9.7 Hz, 1H), 5.52 (t, J=8.0 Hz, 1H), 4.89 (d, J=7.8 Hz, 1H), 4.65 (dd, J=12.1, 2.9 Hz, 1H), 4.50 (dd, J=12.1, 4.9 Hz, 1H), 4.184.15 (m, 1H), 4.064.00 (m, 1H), 3.753.68 (m, 1H), 3.503.46 (m, 6H), 3.36 (t, J=5.2 Hz, 2H), 3.29 (d, J=4.7 Hz, 2H), 2.822.66 (m, 4H), 1.98 (s, 2H), 1.42 (s, 9H); $^{13}$C NMR (75 MHz, CDCl$_3$) $\delta$191.84, 166.14, 165.80, 165.19, 165.10, 133.45, 133.29, 133.25, 133.15, 129.81, 129.75, 129.56, 129.22, 128.76, 128.41, 128.30, 101.43, 79.11, 72.89, 72.24, 71.92, 70.52, 70.19, 70.09, 69.90, 69.69, 63.12, 48.92, 40.34, 28.43; MALDI TOF MS calcd for C$_{47}$H$_{55}$N$_2$O$_{14}$ [M+H]$^+$: 871.36; found: 871.59

Meanwhile, $^1$H NMR and $^{13}$C NMR data of the compounds 6a and 6b are shown in FIGS. 5 to 8.

3. Preparation of [2-(N-Cy3-3,6-dioxaoctane-1,8-diaminoethyl)]-$\alpha$-D-glucose (3) and [2-(N-Cy3-3,6-dioxaoctane-1,8-diaminoethyl)]-$\beta$-D-glucose (4)

(1) [2-(N-Cy3-3,6-dioxaoctane-1,8-diaminoethyl)]-$\alpha$-D-glucose (3)

To a solution of compound 6a (20 mg, 0.023 mmol) in 1 mL of methanol was added sodium methoxide (0.5 M in methanol, 368 µL, 0.184 mmol) for debenzoylation of compound 6a. After the reaction was completed, the mixture was neutralized with methanolic HCl, and then concentrated in vacuo. For the deprotection of Boc group on primary amine, a solution of 50% TFA in dichloromethane was added to the residue, followed by concentration by N$_2$ purging. The resulting fully deprotected compound in DMF (300 µL) was basified with DIPEA and added with Cy3-OH (10 mg, 0.022 mmol) and EDC (7 mg, 0.046 mmol) in 50 µL DMF. The reaction mixture was stirred at room temperature and the reaction was monitored by HPLC analysis. The elution protocol for analytical HPLC starts with 95% water and 5% acetonitrile for 5 min, followed by a linear gradient to 5% water and 95% acetonitrile over 35 min, continued to a linear gradient to 0% water and 100% acetonitrile over 5 min, held at 0% water and 100% acetonitrile for 15 min, and finally returned to 95% water and 5% acetonitrile over 10 min. Purification by prep HPLC affords 5.2 mg (30%) of the desired compound 3 (retention time: 25 min). The desired product was confirmed by $^1$H, $^{13}$C NMR, MALDI-TOF MS, and HRMS.

$^1$H NMR (500 MHz, MeOD) $\delta$8.55 (t, J=13 Hz, 1H), 7.54 (d, J=7.5 Hz, 2H), 7.45 (q, J=7 Hz, 2H), 7.377.29 (m, 5H), 6.43 (d, J=13.5 Hz, 2H), 4.16 (t, J=7.5 Hz, 2H), 4.033.99 (m, 1H), 3.82 (dd, J=11.5, 2.0 Hz, 1H), 3.75 (t, J=4.5 Hz, 2H), 3.69 (s, 5H), 3.66-3.59 (m, 7H), 3.53 (t, J=6.0 Hz, 3H), 3.48 (dd, J=9.5, 3.5 Hz, 1H), 3.36 (t, J=6.0 Hz, 4H), 3.283.26 (m, 4H), 2.30 (t, J=7.0 Hz, 2H), 1.80 (s, 17H); $^{13}$C NMR (125 MHz, MeOD) $\delta$175.56, 174.77, 174.36, 150.96, 142.84, 142.13, 140.97, 128.77, 125.61, 125.52, 122.33, 122.17, 111.17, 111.00, 102.60, 102.39, 99.05, 73.71, 73.11, 72.03, 70.35, 70.20, 70.01, 69.35, 65.63, 62.48, 61.43, 49.42, 43.71, 38.98, 35.04, 30.55, 27.11, 26.93, 26.73, 22.79; HRMS (FAB+): calcd for $C_{43}H_{63}N_4O_9$ [M]$^+$: 779.4595; found, 779.4601.

(2) [2-(N-Cy3-3,6-dioxaoctane-1,8-diaminoethyl)]-β-D-glucose (4)

The same procedure was performed except using compound 6b instead of compound 6a, to obtain compound 4 (7.6 mg, 42%).

$^1$H NMR (500 MHz, MeOD) δ8.58 (t, J=13.5 Hz, 1H), 7.57 (d, J=7.0 Hz, 2H), 7.48 (d, J=4.5 Hz, 2H), 7.39-7.34 (m, 4H), 6.46 (d, J=13.5 Hz, 2H), 4.38 (d, J=7.5 Hz, 1H), 4.19 (t, J=7.0 Hz, 2H), 4.144.11 (m, 1H), 3.973.91 (m, 2H), 3.77 (t, J=5.0 Hz, 2H), 3.723.66 (m, 9H), 3.56 (t, J=5.5 Hz, 2H), 3.403.24 (m, 11H), 2.33 (t, J=6.5 Hz, 2H), 1.79 (s, 17H); $^{13}$C NMR (125 MHz, MeOD) δ175.56, 174.77, 174.36, 150.96, 142.83, 142.13, 140.97, 128.78, 125.62, 125.53, 122.33, 122.17, 111.18, 111.09, 102.97, 102.61, 102.39, 77.02, 76.71, 73.69, 70.33, 70.16, 70.01, 69.36, 65.53, 64.49, 61.36, 49.42, 43.71, 38.97, 35.05, 30.51, 27.11, 26.93, 26.73, 22.79; HRMS (FAB$^+$) calcd for $C_{43}H_{63}N_4O_9$ [M]$^+$: 779.4589; found, 779.4609.

Meanwhile, $^1$H NMR and $^{13}$C NMR data of compounds 3 and 4 are shown in FIGS. 9 to 12.

EXPERIMENTAL EXAMPLE

Purchase of Materials

D-(+)-glucose, acetic anhydride, sodium methoxide (0.5 M solution in methanol), fluorescein isothiocyanate, benzoyl chloride, pyridine, dimethylformamide (DMF), dimethyl sulfoxide (DMSO), and the trifluoroacetic acid (TFA) were purchased from Sigma-Aldrich (St. Louis, Mo., USA). N,N-diisopropylethylamine, triethylamine, and 2-bromoethanol were purchased from TCI (Japan). The $^1$H and $^{13}$C NMR spectra were recorded on a Bruker DRX-300 (Bruker Biospin, Germany) and Varian Inova-500 (Varian Assoc., Palo Alto, USA), and chemical shifts were measured in ppm downfield from internal tetramethylsilane (TMS) standard. The desired products were identified with MALDI-TOF MS analysis using Bruker Daltonics® (Germany). The identity of final compounds was confirmed by high-resolution mass spectrometry (HRMS). HRMS analysis was performed at the Mass spectrometry facility of the National Center for Inter-university Research Facilities, Seoul National University. Reverse phase HPLC analysis was performed on a VP-ODS C-18 column (150×4.6 mm) at a flow rate of 1.0 mL/min for analysis, and PRC-ODS C-18 column (250×20 mm) at a flow rate of 10.0 mL/min for preparation, Shimadzu LC-6AD pump, SPD-10A detector (Japan). HPLC solvents consisted of water containing 0.1% TFA (solvent A) and acetonitrile containing 0.1% TFA (solvent B).

Cell Culture

A549 human lung melanoma cells, HeLa human cervical carcinoma cells, NIH/3T3 murine fibroblast cells, WI-38 human lung fibroblast cells were obtained from American Type Culture Collection (ATCC, Manassas, Va., USA). A549 cells, HeLa cells and WI-38 cells were cultured in RPMI 1640 supplemented with heat-inactivated 10% (v/v) fetal bovine serum (FBS, United Search Partners, Austin, Tex., USA) and 1% (v/v) Antibiotic-Antimycotic solution (United Search Partners, Austin, Tex., USA). NIH/3T3 was cultured in DMEM supplemented with heat-inactivated 10% (v/v) fetal bovine serum and 1% (v/v) antibiotic-antimycotic solution (United Search Partners, Austin, Tex., USA). All the cell lines were maintained in a humidified atmosphere of 5% $CO_2$ and 95% air at 37° C., and cultured in T75 Flask (Nalge Nunc International, Naperville, Ind., USA) in order to observe fluorescence emission by confocal laser scanning microscopy (CLSM).

Protocol of Confocal Laser Scanning Microscope (CLSM)

1×10$^4$ cells were cultured on a Lab-Tek glass chamber slide (Nalge Nunc International, Naperville, Ind., USA) in 35 mm cell culture dish. After 24 h, the glass chamber slide was taken from culture dish and loaded on chamber. Then, the chamber was attached to the microscope. The temperature of the chamber was maintained at 37° C. After injection of 12.5 μM of Cy3-Glc-α in RPMI 1640 in chamber, the fluorescent image was taken every 60 sec, digitalized, and saved on the computer for later analysis.

Protocol of Inverted Fluorescent Microscope

1×10$^4$ cells were cultured on a Lab-Tek glass chamber slide (Nalge Nunc International, Naperville, Ind., USA) in 35 mm cell culture dish. After 24 h, the cells were treated for each experimental purpose. Then, the medium was replaced with RPMI 1640 medium containing 12.5 μM of Cy3-Glc-α. The cells were exposed to Cy3-Glc-α for 40 min, then washed with PBS 3 times. Finally, the glass chamber slide was taken from culture dish and loaded on the fluorescence microscope (Axiovert 200, Carl Zeiss, Germany). Fluorescence images of 35-50 cells were taken by CCD camera (Axiocam MRm, Germany) and fluorescence intensity of each cell was measured by Axiovision (program for data analysis). An area as ROIs (regions of interest) which contains a cell in phase-contrast image was drawn by using Axiovision. Axiovision analyzed CCD camera images and provided the digitalized mean of fluorescence intensity in the ROIs that the present inventors determined. The present inventors subtracted the background intensity from the fluorescence intensity to get the fluorescence intensity value that a cell contained. With the method which is described above, the present inventors digitalized fluorescence intensity and performed various experiments.

EXPERIMENTAL EXAMPLE 1

(1) To evaluate the applicability of the glucose analog according to the present invention that was finally obtained in Example 1 as the bioprobe, first, the uptake efficiency of α-glucose anomer ([2-(N-Cy3-3,6-dioxaoctane-1,8-diaminoethyl)]-α-D-glucose; hereinafter, referred to as "Cy3-Glc-α") into cells was measured by using a confocal laser scanning microscope (CLSM). That is, in order to decide the optimum concentration of the anomer, A549 cells (non-small cell lung cancer cell in human lung carcinoma) were allowed to incorporate the anomer at a concentration of 6 μM, 12.5 μM, 25 μM, 50 μM, and 100 μM.

Figure 13:
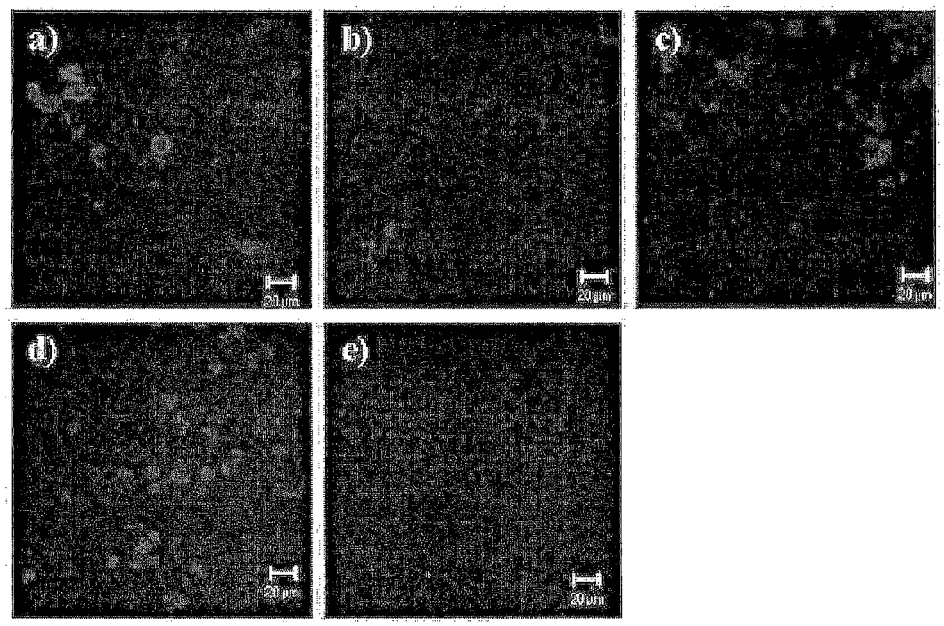
FIG. 13 illustrates pictures uptake efficiency in A549 cells according to the concentration of an α glucose anomer (Cy3-Glc-α) which was taken by using a confocal laser scanning microscope (CLSM) [a) 100 μM, b) 50 μM, c) 25 μM, d) 12.5 μM, and e) 6 μM].

The results are shown in FIG. 13. As shown in FIG. 13, based on the repeated tests, 12.5 μM was selected as the optimum concentration in cellular uptake experiments.

Figure 14:
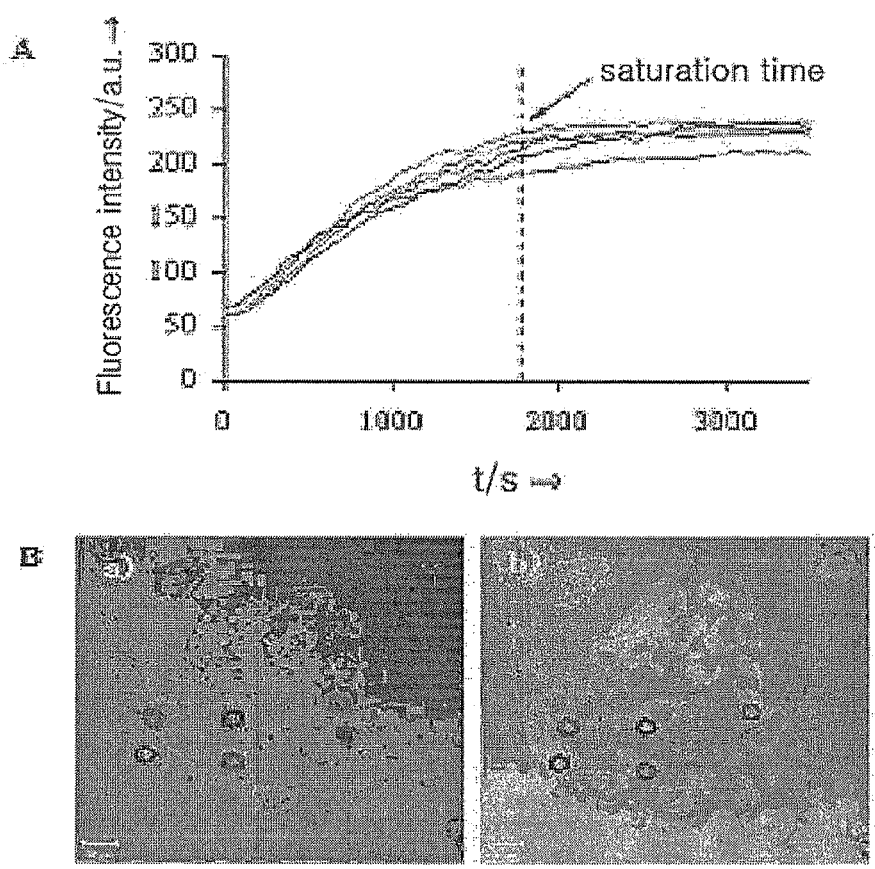
FIG. 14 illustrates the measurement of the uptake efficiency in A549 cells according to the incubation time of an α glucose anomer (Cy3-Glc-α).

(2) In addition, the experiment was performed by using the confocal laser scanning microscope to measure the optimum incubation time required to achieve the maximum uptake of the anomer, Cy3-Glc-α. The results are shown in FIG. 14. As shown in FIG. 14, the uptake of Cy3-Glc-α by A549 cells reached the maximum within 35 min.

Under these optimized conditions, the experiment was performed to confirm whether or not the probe according to the present invention acts as a glucose analog.

EXPERIMENTAL EXAMPLE 2

(1) Compared to 2-NBDG the bioprobe according to the present invention is an O-1-glycosylated glucose analog at the C-1 position; therefore, both anomers were asymmetrically synthesized simultaneously under the assumption that the behavior of these anomers would be different, because the molecular conformations of Cy3-Glc-α and β glucose anomer (hereinafter, referred to as "Cy3-Glc-β") are quite distinct from each other.

Figure 15:
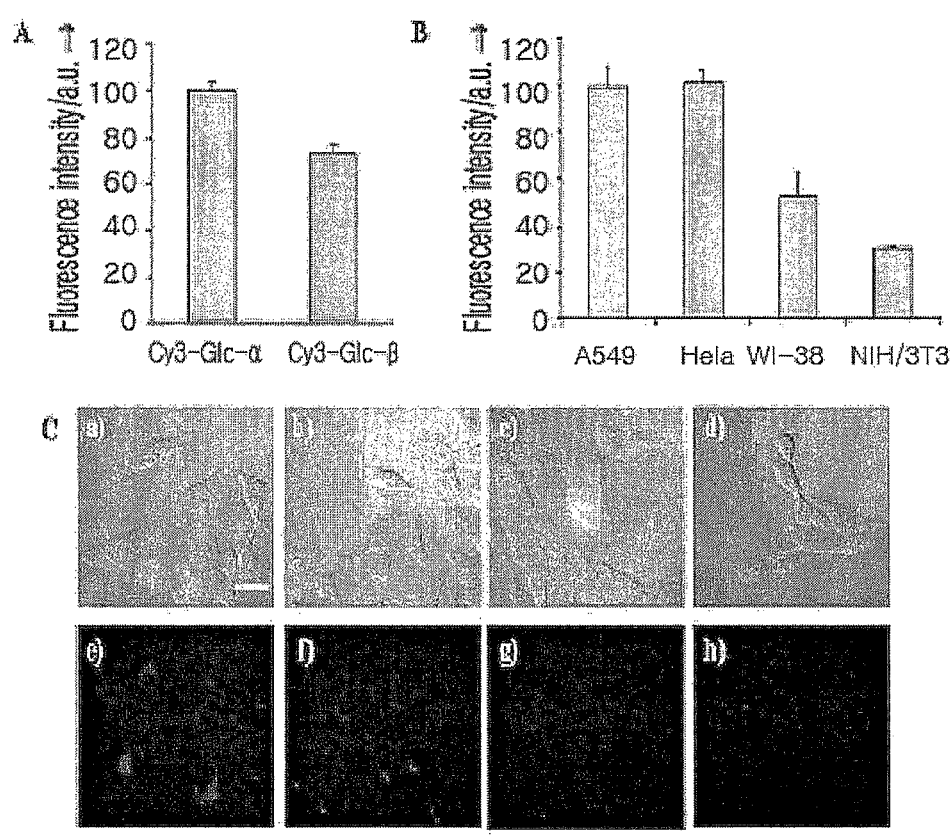
FIG. 15A is a graph that illustrates the Cy3-Glc-α and Cy3-Glc-β uptake by A549 cells. The fluorescence intensities are expressed as an arbitrary unit (a.u.) determined by fluorometry, and data are the mean of 35-50 cells from an experimental representative of at least two independent experiments.
FIG. 15B is a graph that illustrates the efficiency of Cy3-Glc-α uptake in cancer cells (A549, HeLa) and normal cells (WI-38, NIH/3T3).
FIG. 15C illustrates pictures showing the Cy3-Glc-α uptake by A549 cells (a, e), HeLa cells (b, f), WI-38 cells (c, g) and NIH/3T3 cells (d, h). In connection with this, (a-d) are phase-contrast images, and (e-h) are fluorescence images (Scale bar in (a)=40 μm).

To confirm the above hypothesis, real-time uptake of Cy3-Glc-α was measurement, and the results were compared to those of Cy3-Glc-β by live imaging of A549 cells by using inverted fluorescent microscope. As shown in FIG. 15A, the uptake of Cy3-Glc-α was 40% superior to that of Cy3-Glc-β. This led the present inventors to the conclusion that the stereochemistry at the C-1 anomeric position definitely influences the efficiency of mimicking glucose, and this might be due to the binding orientation of D-glucose in GLUTs [P. W. Hruz, M. M. Mueckler, *Mole. Memb. Biol.* 2001, 18, 183-193].

(2) Based on this observation, further studies in bioimaging and bioapplication were performed only with the α anomer as choice of the bioprobe. That is, the efficiency of Cy3-Glc-α uptake was measured, in particular, the differentiation of GLUT-overexpressing cancer cells (A549; lung carcinoma cell line, HeLa; cervical carcinoma cell line) was preponderantly tested instead of normal cells (WI-38; lung normal cell line, NIH/3T3; murine fibroblast cell line).

As shown in FIG. 15B, Cy3-Glc-α uptake in NIH/3T3 was only 30% that of A549 cells. Accordingly, the selective uptake of Cy3-Glc-α in cancer cells with enhanced glucose-metabolism was confirmed. This data demonstrated that the cellular uptake of Cy3-Glc-α depends on the higher glucose metabolism in cancer cells, which in turn relies on the ATP generated from glycolysis in order to meet the energy requirements of rapidly replicating tissue. Therefore, glucose metabolism is strongly correlated with the GLUT/hexokinase expression levels. From the data, it could be seen that Cy3-Glc-α according to the present invention was capable of being applied to molecular bioimaging and bioassay in cancer studies.

Meanwhile, FIG. 15C is a picture that illustrates the uptake of Cy3-Glc-α by A549 cells (a, e), HeLa cells (b, f), WI-38 cells (c, g) and NIH/3T3 cells (d, h).

EXPERIMENTAL EXAMPLE 3

To confirm whether the intracellular uptake pathway of glucose analogs is relevant to that of D-glucose, the direct competition experiment has been utilized in many studies [M. Zhang, Z. Zhang, D. Blessington, H. Li, T. M. Busch, V. Madrak, J. Miles, B. Chance, J. D. Glickson, U Zheng, *Bioconjugate Chem.* 2003, 14, 70-97; K. Yamada, M. Nakata, N. Horimoto, M. Saito, H. Matsuoka, N. Inagaki, *J. Biol. Chem.* 2000, 275, 22278-22283]. If the cellular uptake of a certain glucose analog depends on the concentration of D-glucose but not on that of L-glucose, then that the particular glucose analog would enter the cell via a GLUT-mediated glucose uptake system.

Therefore, based on prior experiments, the process of the cellular uptake of Cy3-Glc-α was tested. The test was performed by measuring the efficiency of Cy3-Glc-α uptake by A549 cells in RPMI 1640 lacking glucose or containing 10 mM D-glucose, 50 mM D-glucose, and 50 mM L-glucose (37° C.).

Figure 16:
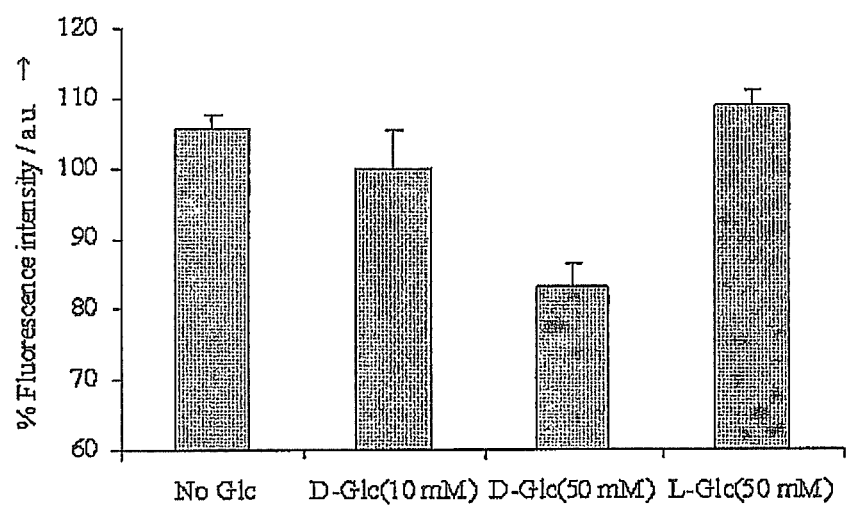
FIG. 16 is a graph that illustrates dose-dependent Cy3-Glc-α uptake inhibition in A549 cells when there is no glucose, 10 mM D-glucose or 50 mM D-glucose. To demonstrate specific inhibition by D-glucose, an identical experiment was performed in the presence of 50 mM L-glucose, which does not result in uptake inhibition. The fluorescence intensities are expressed as arbitrary units (a.u.) determined by the fluorometry, and the data are the mean of 35-50 cells from an experimental representative of at least two independent experiments.

As shown in FIG. 16, the uptake of Cy3-Glc-α decreased as the concentration of D-glucose in the medium increased. However, the uptake of Cy3-Glc-α was not influenced by the concentration of L-glucose in the medium. This suggests that Cy3-Glc-α is taken up by the cell through a glucose-specific transport system, not by passive diffusion. Therefore, Cy3-Glc-α can function as a D-glucose analog and can be applied as a research tool in the study of glucose metabolism.

EXPERIMENTAL EXAMPLE 4

Figure 17:
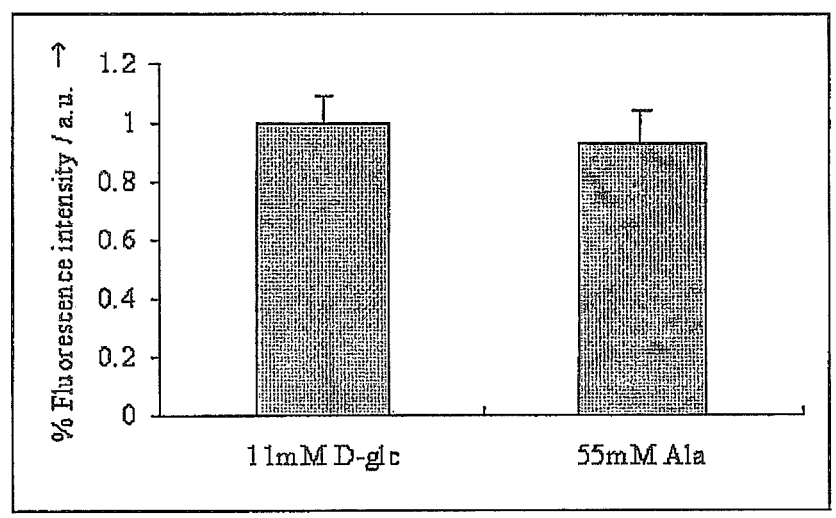
FIG. 17 is a graph that illustrates the uptake of Cy3-Glc-α using A549 cells in the absence or presence of 55 mM alanine.

In addition, the uptake of Cy3-Glc-α was measured using A549 cells in media containing 55 mM alanine in order to ensure that the osmotic pressure in the medium does not affect the uptake of Cy3-Glc-α. As shown in FIG. 17, there was no difference in the uptake efficiency under the media with or without 55 mM alanine. This demonstrates the fact that the osmotic pressure does not affect the uptake of Cy3-Glc-α by A549.

EXPERIMENTAL EXAMPLE 5

It was confirmed that Cy3-Glc-α acted as a D-glucose analog, and Cy3-Glc-α was compared to a fluorescent analog of 2-deoxyglucose, for example, 2-NBDG [M. Zhang, Z. Zhang, D. Blessington, H. Li, T. M. Busch, V. Madrak, J. Miles, B. Chance, J. D. Glickson, G Zheng, *Bioconjugate Chem.* 2003, 14, 7097; K. Yoshioka, H. Takahashi, T. Homma, M. Saito, K. B. Oh, Y. Nemoto, H. Matsuoka, *Biochim. Biophys. Acta.* 1996, 1289, 5-9; K. Yoshioka, M. Saito, K. B. Oh, Y. Nemoto, H. Matsuoka, M. Natsume, H. Abe, *Biosci. Biotech. Biochem.* 1996, 60, 1899-1901].

The cellular uptake of 2-NBDG was not detected under the identical experimental condition of Cy3-Glc-α. Even when 125 μM of 2-NBDG was exposed to the lens of CCD camera for 500 ms, the fluorescence was not detected. To achieve the fluorescence intensity with 2-NBDG to 80% that of Cy3-Glc-α, 10 fold increase of 2-NBDG concentration and 20 fold increase of lens exposure time in D-glucose-depleted medium were needed.

Figure 18:
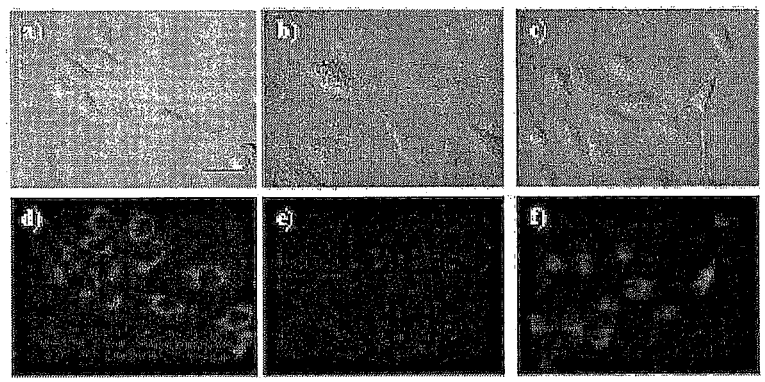
FIG. 18 illustrates the uptake image of 2-NBDG and Cy3-Glc-α by the A549 cells with different conditions. (a, d) are pictures that illustrate 12.5 μM of Cy3-Glc-α with lens exposure of the CCD camera for 500 ms. (b, e) are pictures that illustrate 12.5 μM of 2-NBDG with lens exposure of the CCD camera for 500 ms. (c, f) are pictures that illustrate 125 μM of 2-NBDG with lens exposure of CCD camera for 11000 ms. (a, b, c) illustrate the phase-contrast images in the A549 cells. (d, e, f) illustrate the fluorescence images in the A549 cells (Scale bar in (a)=40 μm).

In addition, the cellular uptake of 2-NBDG in normal media (containing 10 mM D-glucose) was extremely low (>60% uptake reduction in normal media) and was hardly detected using fluorescent based imaging methods [R. G O'Neil, L. Wu, N. Mullani, *Mol. Imaging. Biol.* 2005, 7, 388-392]. 2-NBDG was detectable only in glucose-depleted media, and this means a critical limitation of bioapplication of 2-NBDG in the biologically significant environments. In comparison with 2-NBDG, the reduction of Cy3-Glc-α uptake in glucose-containing media was only 5% compared to that in glucose-depleted media (FIG. 18). Therefore, it was confirmed that Cy3-Glc-α was capable of being applied to a bioassay system regardless of glucose starvation.

EXPERIMENTAL EXAMPLE 6

(1) Based on the fact that Cy3-Glc-α could be taken up by cells as a D-glucose analog through a D-glucose specific transport mechanism in normal glucose-containing medium, Cy3-Glc-α was applied to the screening of small molecular modulators involved in cellular metabolism. The application was performed under the postulation that the depression of perturbed cellular metabolism in cancer cells was caused by anticancer agents, which was closely related to the reduction of glucose uptake.

The present inventors intended to monitor this phenomenon by the fluorescent bioprobe according to the present invention, that is, Cy3-Glc-α. As a proof-of-principle experiment, after A549 cancer cells were treated with taxol (9.8 μM), an anticancer agent, and the uptake of Cy3-Glc-α was measured at 3, 6, 12, and 24 h after the treatment.

Figure 19:
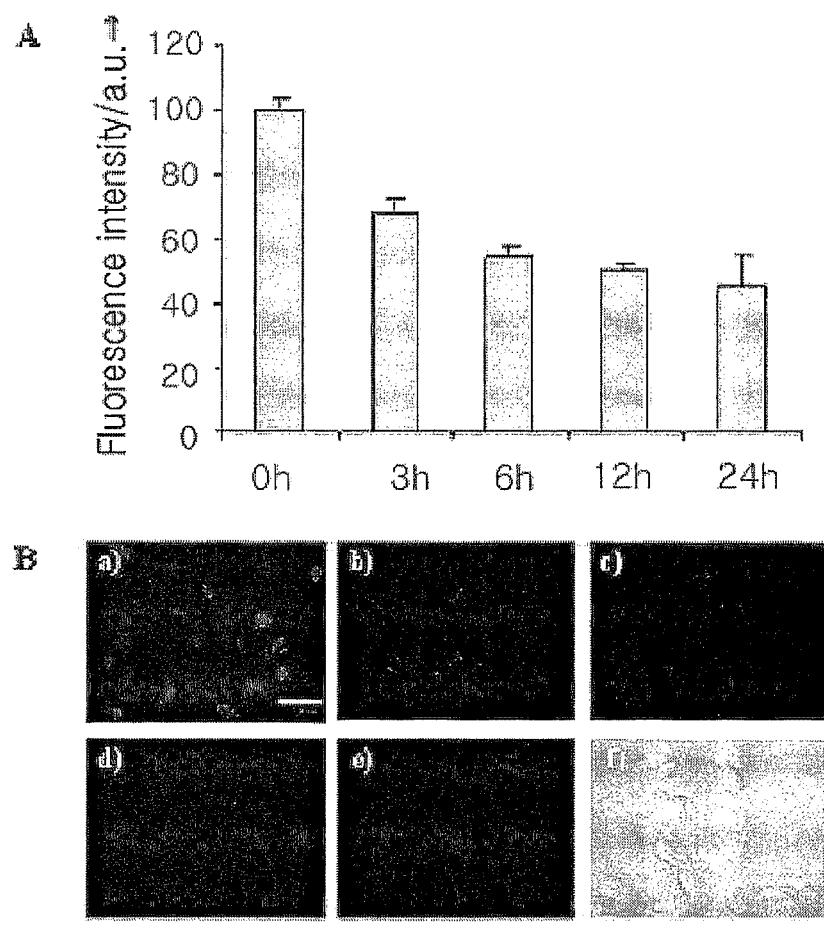
FIG. 19A is a graph that illustrates the Cy3-Glc-α uptake by A549 cells measured after 0, 3, 6, 12, and 24 h of treatment with taxol (9.8 μM) at 37° C. In connection with this, the fluorescence intensities are expressed as an arbitrary unit (a.u.) determined by fluorometry and the data are the mean of 35-50 cells from an experimental representative of at least two independent experiments.
FIG. 19B illustrates images showing the Cy3-Glc-α uptake by A549 cells after treatment with taxol (9.8 μM) at 37° C. for the following durations (a; 0 h, b; 3 h, c; 6 h, d; 12 h, e; 24 h, and f; phase-contrast image after 6 h incubation. After incubation with treatment of taxol, each image was captured with a fluorescent microscope after 30 min of Cy3-Glc-α treatment (Scale bar in (a)=40 μm).

As shown in FIG. 19, the cellular uptake of the probe reduced as the incubation time increased. This clearly demonstrates the potential of Cy3-Glc-α for evaluation of the metabolic perturbation caused by bioactive small molecules in live cells under physiological conditions.

Figure 20:
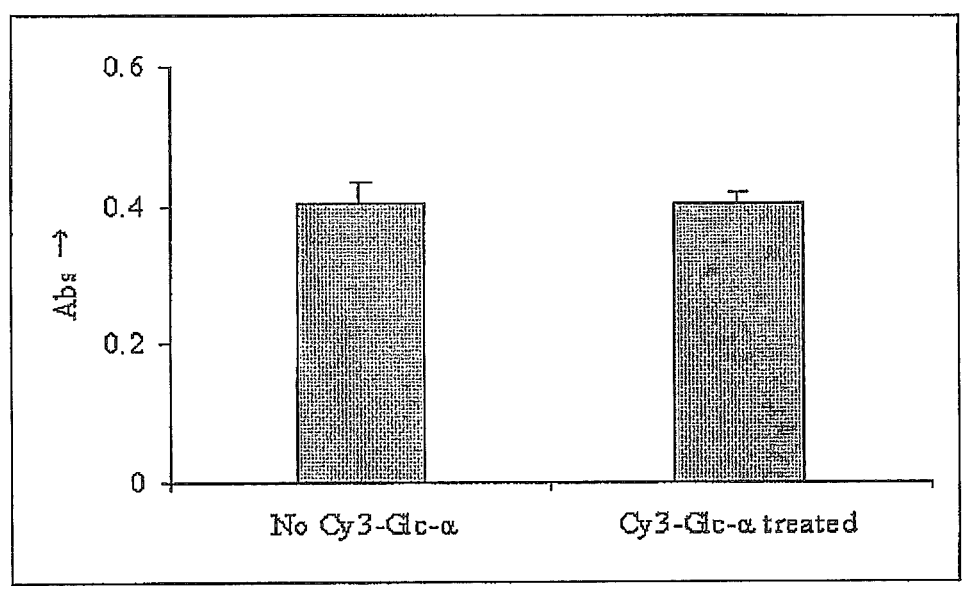
FIG. 20 is a graph that illustrates the measurement of the viability of cells treated with Cy3-Glc-α (12.5 μM) by using a CCK-8 kit.

(2) Therefore, Cy3-Glc-α should not affect cell viability. The viability of cells treated with Cy3-Glc-α (12.5 μM) by using a CCK-8 kit (Cell Counting Kit-8, Dojindo, Japan) was measured by using an ELISA plate reader (ELx800™, Bio-Tex, USA) DP. CCK-8 is a colorimetric assay for determining the number of viable cells in cell proliferation and cytotoxicity assays. The principle of measuring cell viability of CCK-8 is the same as that of MIT. However, CCK-8 is more sensitive than MTT. Hence the present inventors selected CCK-8 for cell viability test. With the result by CCK-8, as shown in FIG. 20, the present inventors could conclude that Cy3-Glc-α treatment does not affect cell viability in the present incubation condition.

(3) In addition, after the taxol concentration was changed in the range of 490 nM to 49 nM, the uptake of Cy3-Glc-α by A549 cells was measured after 8 hr and 12 hr, and after another anticancer agent, i.e., combretastatin, (2 μM) was treated in A549 cells, the uptake of Cy3-Glc-α by A549 cells was measured after 8 hr and 12 hr.

From the following Table 1, it could be seen that the uptake of Cy3-Glc-α by A549 cells depended on the dose. In addition, combretastatin inhibited the multiplication of cells by obstructing cell metabolism, which could be seen by the reduction in the cellular uptake of Cy3-Glc-α.

TABLE 1

|  | 6 h | 12 h |
| --- | --- | --- |
| Taxol (9.8 μM) | 54.8% | 50.2% |
| Taxol (490 nM) | 88.4% | 61.8% |
| Taxol (49 nM) | 96.5% | 86.9% |
| Combretastatin (2 μM) | 57.4% | 45.0% |

Based on the above experiments, it is deemed that Cy3-Glc-α can be used to evaluate the behavior of bioactive small molecules in cells in a manner similar to the MTT assay [T. Mosmann, *J. Immunol. Methods.* 1983, 65, 55-63], which measures the mitochondrial function. The advantages of a screening system with Cy3-Glc-α over an MTT assay are as follows: first, the measurement time is short. MTT assays usually take 24 hours and up to 72 hours in many cases, e.g. when taxol and combretastatin are used; whereas the screening system with Cy3-Glc-α showed significant difference in that it takes 6 hours to 12 hours. Second, the observation channel of a screening system with Cy3-Glc-α is quite different from that of a cell-viability assay, that is, the former involves measuring glucose-uptake efficiency, and the latter involves measuring mitochondria function. Therefore, it is deemed that the two assay systems will compensate for limitations of each other.

The invention claimed is:

1. A molecular bioimaging method using a fluorescent dye-labeled glucose analog that is represented by Formula 1 or Formula 2 as a bioprobe:

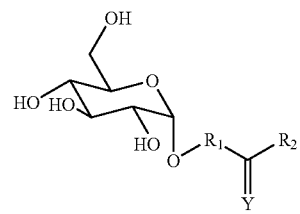

[Formula 1]

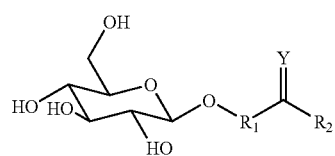

[Formula 2]

wherein $R_1$ is —$(CH_2)_n$—NH—$(C_2H_4X)_m$—NH—, n is an integer in the range of 1 to 10, m is an integer in the range of 1 to 100, X is $CH_2$, O or a single bond, and Xs may be the same as or different from each other when m is 2 or more, $R_2$ is Cy3, and Y is O or S.

2. The molecular bioimaging method as set forth in claim 1, wherein the molecular bioimaging method is performed by using a confocal laser scanning microscope (CLSM), an inverted fluorescent microscope, a fluorescent activated cell sorter (FACS), a microplate reader, or a high content screening as a measuring device.

3. The molecular bioimaging method as set forth in claim 1, wherein the molecular bioimaging method is used for cancer or tumor imaging or examination of glucose transporters-related cell metabolism.

4. The molecular bioimaging method as set forth in claim 1, wherein the glucose analog is used at a concentration in the range of 1 to 100 μM and cultured for 35 minutes or less.

* * * * *